United States Patent
Pulé

(10) Patent No.: US 12,209,114 B2
(45) Date of Patent: Jan. 28, 2025

(54) CHIMERIC ANTIGEN RECEPTOR

(71) Applicant: UCL BUSINESS LTD, London (GB)

(72) Inventor: Martin Pulé, London (GB)

(73) Assignee: UCL BUSINESS LTD, London (GB)

( * ) Notice: Subject to any disclaimer, the term of this patent is extended or adjusted under 35 U.S.C. 154(b) by 1027 days.

(21) Appl. No.: 17/250,053

(22) PCT Filed: May 15, 2019

(86) PCT No.: PCT/GB2019/051329
§ 371 (c)(1),
(2) Date: Nov. 13, 2020

(87) PCT Pub. No.: WO2019/220108
PCT Pub. Date: Nov. 21, 2019

(65) Prior Publication Data
US 2021/0309716 A1    Oct. 7, 2021

(30) Foreign Application Priority Data
May 15, 2018 (GB) ...................... 1807862

(51) Int. Cl.
C07K 14/705 (2006.01)
A61K 38/00 (2006.01)
A61K 39/00 (2006.01)
A61K 45/06 (2006.01)
C07K 16/28 (2006.01)
C12N 5/0783 (2010.01)

(52) U.S. Cl.
CPC .... *C07K 14/70596* (2013.01); *A61K 39/4611* (2023.05); *A61K 39/4631* (2023.05); *A61K 39/464402* (2023.05); *A61K 39/464412* (2023.05); *A61K 45/06* (2013.01); *C07K 16/2896* (2013.01); *C12N 5/0636* (2013.01); *A61K 38/00* (2013.01); *C07K 2317/565* (2013.01); *C07K 2317/567* (2013.01); *C07K 2317/622* (2013.01); *C07K 2319/02* (2013.01); *C07K 2319/03* (2013.01); *C07K 2319/30* (2013.01); *C07K 2319/33* (2013.01)

(58) Field of Classification Search
None
See application file for complete search history.

(56) References Cited

U.S. PATENT DOCUMENTS 7,052,906 B1   5/2006   Lawson et al.

FOREIGN PATENT DOCUMENTS

| WO | WO-2017027291 A1 * | 2/2017 | ........... A61K 31/138 |
| WO | WO-2017149515 A1 * | 9/2017 | ............ A61K 35/17 |
| WO | WO-2017211900 A1 * | 12/2017 | ............ A61K 35/17 |
| WO | WO-2018/193231 A1 | 10/2018 | |

OTHER PUBLICATIONS

Bedouelle et al. Fees J. Jan. 2006;273(1):34-46 (Year: 2006).*
Rudikoff et al. Proc. Natl. Acad. Sci. 1982. 79: 1979-1983 (Year: 1982).*
Vajdos et al. J Mol Biol. Jul. 5, 2002;320(2):415-28 (Year: 2002).*
International Application No. PCT/GB2019/051329, International Search Report and Written Opinion, mailed Jul. 13, 2019.
Ljungars et al., A platform for phenotypic discovery of therapeutic antibodies and targets applied on Chronic Lymphocytic Leukemia, npj Precision Oncology, 2, Article No. 18 (2018).
Lopez-Matas et al., Quantitative expression of CD23 and its ligand CD21 in chronic lymphocytic leukemia, Haematologica, 85(11):1140-5 (2000).
Pinchot et al., Identification and validation of Notch pathway activating compounds through a novel high-throughput screening method, Cancer, 117(7):1386-98 (2011).
Shepherd et al., PI3K/mTOR inhibition upregulates NOTCH-MYC signalling leading to an impaired cytotoxic response, Leukemia, 27(3):650-60 (2013).
Shi et al., CD21 and CD23 expression differences in small B-cell lymphomas: comparative analysis in follicular dendritic cells and tumor cells, Int. J. Clin. Exp. Pathol., pp. 8395-8405 (2016).
Tatsumi et al., CD21 antigen in T-lineage neoplastic lymphoid cells: characteristic expression at thymic stage, Am. J. Hematol., 45(2):150-5 (1994).
Van Vlierberghe et al., The molecular basis of T cell acute lymphoblastic leukemia, J. Clin. Invest., 122(10):3398-406 (2012).

\* cited by examiner

*Primary Examiner* — Zachary S Skelding
*Assistant Examiner* — Brianna K Swartwout
(74) *Attorney, Agent, or Firm* — MARSHALL, GERSTEIN & BORUN LLP

(57) ABSTRACT

The present invention provides a chimeric antigen receptor (CAR) comprising a CD21-binding domain, a transmembrane domain and an intracellular domain.

15 Claims, 10 Drawing Sheets

Specification includes a Sequence Listing.

CHIMERIC ANTIGEN RECEPTOR

FIELD OF THE INVENTION

The present invention relates to a chimeric antigen receptor (CAR).

BACKGROUND TO THE INVENTION

Despite recent progress in survival rates, T-cell acute lymphocytic leukaemia (T-ALL) remains a challenging clinical problem. Long-term survival is poor for adult patients, and the outlook is particularly poor for patients of all ages with relapsed/refractory disease.

Chimeric Antigen Receptors (CARs) are synthetic signalling molecules which redirect immune effector cells, for example T-cells, to kill tumours expressing a surface target antigen. CAR T-cells against CD19 are revolutionising the treatment of children with relapsed/refractory B-acute lymphoblastic leukaemia and adults with diffuse large B-cell lymphoma. In recent clinical studies of paediatric B-ALL, remission rates close to 100% have been reported, with ~60% of patients achieving sustained responses. However, some 15% of paediatric and 20-25% of adult cases of ALL are of T-lineage (T-ALL), and are therefore not suitable for treatment with anti-CD19 therapy. No other novel therapies are available, and prognosis for patients with T-ALL who have failed standard intensive chemotherapy is poor.

Development of immunotherapy for T-ALL is challenging for multiple reasons. Targeting CD19, a pan B-cell antigen, results in concomitant loss of the normal B-cell compartment. However, this is reasonably well tolerated and is an acceptable toxicity which if needed can be mitigated by pooled immunoglobulins. In contrast, targeting a pan-T-cell antigen results in profound unacceptable immunosuppression which cannot be mitigated. In addition, CAR T-cell production would be limited by fratricide of normal T-cells expressing the target molecule. Therefore, all antigens investigated to date for treatment of T-ALL (CD36, CD47, CD58, CD79) could only be at best a bridge to bone marrow transplantation.

Accordingly, there remains a need for novel therapeutic approaches to cancers such as leukaemias, in particular T-ALL.

SUMMARY OF THE INVENTION

The present inventors have developed novel binding molecules against CD21. These binding molecules have been developed for use in the context of a CAR.

Accordingly, in a first aspect the present invention provides a chimeric antigen receptor (CAR) comprising a CD21-binding domain, a transmembrane domain and an intracellular domain.

The CD21-binding domain may be a scFv.

The CD21-binding domain may comprise a heavy chain variable region (VH) which comprises a complementary determining region (CDR) selected from SEQ ID NO: 4, 6, 9, 12 and 14 or a variant thereof with up to three amino acid substitutions.

The CD21-binding domain comprises a light chain variable region (VL) may comprise a CDR selected from SEQ ID NO: 17, 20, 23, 26, and 29 or a variant thereof with up to three amino acid mutations.

The CD21-binding domain may comprise six CDRs selected from (I) to (vi) as follows: (i) SEQ ID NOs: 2 to 4 and 15 to 17 or variants thereof with up to three amino acid substitutions in each CDR; (ii) SEQ ID NOs: 2, 5, 6 and 18 to 20 or variants thereof with up to three amino acid substitutions in each CDR; (iii) SEQ ID NOs: 7 to 9 and 21 to 23 or variants thereof with up to three amino acid substitutions in each CDR; (iv) SEQ ID NOs: 7 to 9 and 24 to 26 or variants thereof with up to three amino acid substitutions in each CDR; (v) SEQ ID NOs: 10 to 12 and 27 to 29 or variants thereof with up to three amino acid substitutions in each CDR in each CDR; and (vi) SEQ ID NOs: 2, 13, 14, 21, 57 and 23 or variants thereof with up to three amino acid mutations in each CDR.

The CD21-binding domain may comprises six CDRs selected from (i) to (vi) as follows: (i) SEQ ID NOs: 2 to 4 and 15 to 17; (i) SEQ ID NOs: 2, 5, 6 and 18 to 20; (Ili) SEQ ID NOs: 7 to 9 and 21 to 23; (iv) SEQ ID NOs: 7 to 9 and 24 to 26; (v) SEQ ID NOs: 10 to 12 and 27 to 29; and (vi) SEQ ID NOs: 2, 13, 14, 21, 57 and 23.

The six CDR sequences may be grafted onto a human antibody framework sequence.

The CD21-binding domain may comprise an amino acid sequence shown as any one of SEQ ID NO: 30-37 or 58 or a variant of any one of SEQ ID NO: 30-37 or 58 having at least 80% sequence identity thereto.

The intracellular domain may comprise a T cell signalling domain.

In a further aspect the present invention provides polynucleotide which encodes a CAR according to the first aspect of the invention.

In another aspect the present invention provides a vector which comprises a polynucleotide according to the present invention.

In a further aspect the present invention provides a cell expressing a CAR according to the present invention.

The cell may be an alpha-beta T cell, a NK cell, a gamma-delta T cell, or a cytokine induced killer cell.

In a further aspect the present invention relates to a pharmaceutical composition which comprises a CAR; a polynucleotide; a vector or a cell according to the present invention.

In another aspect the present invention relates to a pharmaceutical composition according to the invention for use in treating and/or preventing a disease.

In a further aspect the present invention relates to a method for treating and/or preventing a disease, which comprises the step of administering a pharmaceutical composition according to the invention to a subject in need thereof.

The method may comprise the following steps:
(i) isolation of a cell containing sample;
(ii) transduction or transfection of the cell with a polynucleotide or a vector according to the invention; and
(iii) administering the cells from (ii) to a subject.

The cell may be autologous or allogenic.

The invention further relates to the use of a pharmaceutical composition of the invention in the manufacture of a medicament for the treatment and/or prevention of a disease.

The disease may be T-cell acute lymphoblastic leukaemia.

The disease may be a B-cell cell leukaemia or a B-cell lymphoma.

The pharmaceutical composition of the invention may be administered in combination with a NOTCH activating agent.

The NOTCH activating agent may be, for example, a PI3K inhibitor, an AKT inhibitor and/or a mTOR inhibitor.

The pharmaceutical composition of the invention and the NOTCH activating agent may be administered simultaneously, sequentially or separately.

In a further aspect the present invention provides a kit comprising (i) a CAR, a polynucleotide; a vector; a cell or a pharmaceutical composition according to the invention; and (ii) a NOTCH activating agent.

DETAILED DESCRIPTION OF THE INVENTION

In one aspect, the present invention relates to a CAR comprising a CD21-binding domain, a transmembrane domain and an intracellular domain.

CD21

CD21/Complement receptor type 2 (CR2) (also known as complement C3d receptor and Epstein-Barr virus receptor), is a protein that in humans is encoded by the CR2 gene.

CD21 is involved in the complement system. It binds to iC3b (inactive derivative of C3b), C3dg, or C3d. B cells have CD21 on their surfaces, allowing the complement system to play a role in B-cell activation and maturation.

The present inventors have determined that CD21 may be expressed in T-cell acute lymphomablastic leukaemia (T-ALL) and that CD21 is not expressed on normal non-lymphoid tissue (see present Example 2). Tatsumi et al. have also reported CD21 expression in T-ALL (*Am J Hematol* 45, 150-155 (1994)).

Thus, without wishing to be bound by theory, a CAR targeting CD21 may result in B cell depletion (as seen in CD19-targeted CAR therapy) but no other significant haematological toxicity.

An illustrative human CD21 protein is provided by UniProt Accession Number P20023, the amino acid sequence of which is shown as SEQ ID NO: 1.

```
                                            SEQ ID NO: 1
MGAAGLLGVFLALVAPGVLGISCGSPPPILNGRISYYSTPIAVGTVIRY

SCSGTFRLIGEKSLLCITKDKVDGTWDKPAPKCEYFNKYSSCPEPIVPG

GYKIRGSTPYRHGDSVTFACKINFSMNGNKSVWCQANNMWGPTRLPTCV

SVFPLECPALPMIHNGHHTSENVGSIAPGLSVTYSCESGYLLVGEKIIN

CLSSGKWSAVPPTCEEARCKSLGRFPNGKVKEPPILRVGVIANFFCDEG

YRLQGPPSSRCVIAGQGVAWTKMPVCEEIFCPSPPPILNGRHIGNSLAN

VSYGSIVTYTCDPDPEEGVNFILIGESTLRCTVDSQKIGTWSGPAPRCE

LSTSAVQCPHPQILRGRMVSGQKDRYTYNDTVIFACMFGFTLKGSKQIR

CNAQGTWEPSAPVCEKECQAPPNILNGQKEDRHMVRFDPGISIKYSCNP

GYVLVGEESIQCTSEGVWTPPVPQCKVAACEATGRQLLTKPQHQFVRPD
```

-continued

```
VNSSCGEGYKLSGSVYQECQGTIPWFMEIRLCKEITCPPPPVIYNGAHT

GSSLEDFPYGTTVTYTCNPGPERGVEFSLIGESTIRCTSNDQERGTWSG

PAPLCKLSLLAVQCSHVHIANGYKISGKEAPYFYNDTVTFKCYSGFILK

GSSQIRCKADNTWDPEIPVCEKETCQHVRQSLQELPAGSRVELVNTSCQ

DGYQLIGHAYQMCQDAENGIWFKKIPLCKVIHCHPPPVIVNGKHIGMMA

ENFLYNEVSYECDQGFYLLGEKKLQCRSDSKGHGSWSGPSPQCLRSPPV

TRCPNPEVKHGYKLNKTHSAYSHNDIVYVDCNPGFIMNGSRVIRCHIDN

IWVPGVPTCIKKAFIGCPPPPKIPNGNHIGGNIARFSPGMSILYSCDQG

YLLVGEALLLCTHEGTWSQPAPHCKEVNCSSPADMDGIQKGLEPRKMYQ

YGAVVTLECEDGYMLEGSPQSQCQSDHQWNPPLAVCRSRSLAPVLCGIA

AGLILLTFLIVITLYVISKHRARNYYTDTSQKEAFHLEAREVYSVDPYN

PAS
```

Chimeric Antigen Receptor (Car)

Figure 1:
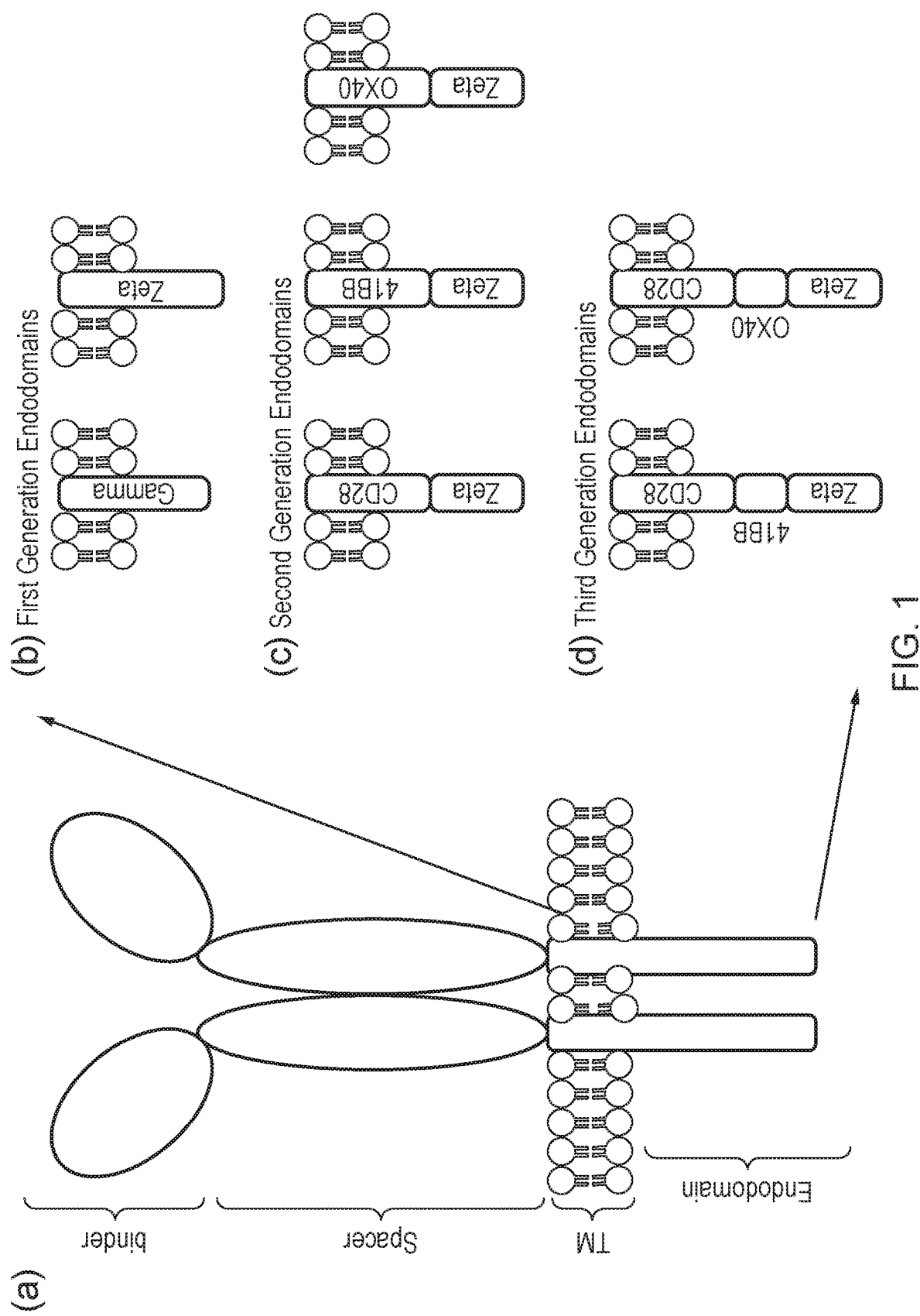
FIG. 1—a) Schematic diagram illustrating a classical CAR. (b) to (d): Different generations and permutations of CAR endodomains: (b) initial designs transmitted ITAM signals alone through FcεR1-γ or CD3ζ endodomain, while later designs transmitted 25 additional (c) one or (d) two co-stimulatory signals in the same compound endodomain.

Classical CARs, which are shown schematically in FIG. 1, are chimeric type I trans-membrane proteins which connect an extracellular antigen-binding domain (binder) to an intracellular signalling domain (endodomain). The binder is typically a single-chain variable fragment (scFv) derived from a monoclonal antibody (mAb), but it can be based on other formats which comprise an antibody-like antigen binding site or on a ligand for the target antigen. A spacer domain may be necessary to isolate the binder from the membrane and to allow it a suitable orientation. A common spacer domain used is the Fc of IgG1. More compact spacers can suffice e.g. the stalk from CD8a and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 4-1BB which transmit survival signals. Even more potent third generation CARs have now been described which have endodomains capable of transmitting activation, proliferation and survival signals.

CAR-encoding nucleic acids may be transferred to T cells using, for example, retroviral vectors. In this way, a large number of antigen-specific T cells can be generated for adoptive cell transfer. When the CAR binds the target-antigen, this results in the transmission of an activating signal to the T-cell it is expressed on. Thus the CAR directs the specificity and cytotoxicity of the T cell towards cells expressing the targeted antigen.

Antigen Binding Domain

The antigen-binding domain is the portion of a classical CAR which recognizes antigen.

Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain binder such as a camelid; an artificial binder single as a Darpin; or a single-chain derived from a T-cell receptor.

The antigen-binding domain may be a polypeptide having an antigen binding site which comprises at least one complementarity determining region (CDR). The antigen-binding domain may comprise 3 CDRs and have an antigen binding site which is equivalent to that of a domain antibody (dAb). The antigen-binding domain may comprise 6 CDRs and have an antigen binding site which is equivalent to that of a classical antibody molecule. The remainder of the polypeptide may be any sequence which provides a suitable scaffold for the antigen binding site and displays it in an appropriate manner for it to bind the antigen. The antigen-binding domain may be part of an immunoglobulin molecule such as a Fab, F(ab)'$_2$, Fv, single chain Fv (ScFv) fragment, Nanobody or single chain variable domain (which may be a VH or VL chain, having 3 CDRs). The antigen-binding domain may be non-human, chimeric, humanised or fully human.

The antigen-binding domain may comprise a binding domain which is not derived from or based on an immunoglobulin. A number of "antibody mimetic" designed repeat proteins (DRPs) have been developed to exploit the binding abilities of non-antibody polypeptides. Such molecules include ankyrin or leucine-rich repeat proteins e.g. DARPins (Designed Ankyrin Repeat Proteins), Anticalins, Avimers and Versabodies.

The binding domain may "specifically bind" to the antigen as defined herein. As used herein, "specifically bind" means that the binding domain binds to the antigen but does not bind to other peptides, or binds at a lower affinity to other peptides.

The binding affinity between two molecules, e.g. an antigen binding domain and an antigen, may be quantified, for example, by determination of the dissociation constant (KD). The KD can be determined by measurement of the kinetics of complex formation and dissociation between the antigen-binding domain and antigen, e.g. by a surface plasmon resonance (SPR) method (e.g. Biacore). The rate constants corresponding to the association and the dissociation of a complex are referred to as the association rate constants ka (or kon) and dissociation rate constant kd. (or koff), respectively. KD is related to ka and kd through the equation KD=kd/ka.

Binding affinities associated with different molecular interactions, e.g. comparison of the binding affinity of different antigen-binding domains and an antigen, may be compared by comparison of the KD values for the individual antigen-binding domain and antigen.

The present invention provides a CAR comprising a CD21-binding domain.

The CD21-binding domain may be based on a CD21 binder as shown in Tables 1 and 2.

TABLE 1

Variable Heavy Chain Usage + CDRs

Variable Heavy Chain Usage

| Clone | CDR1 | CDR2 | CDR3 |
|---|---|---|---|
| MP27963 | GYTFTSN (SEQ ID NO: 2) | SPGDGD (SEQ ID NO: 3) | GDSSGWGPNWFDS (SEQ ID NO: 4) |
| MP27964 | GYTFTSN (SEQ ID NO: 2) | YPGDGD (SEQ ID NO: 5) | SGDGYFDY (SEQ ID NO: 6) |
| MP27965 | GYTFTTN (SEQ ID NO: 7) | NPGDGN (SEQ ID NO: 8) | GDYSGWGPNWFDY (SEQ ID NO: 9) |
| MP27966 | GYTFTTN (SEQ ID NO: 7) | NPGDGN (SEQ ID NO: 8) | GDYSGWGPNWFDY (SEQ ID NO: 9) |
| MP27967 | GYNIRNT (SEQ ID NO: 10) | DPANGDT (SEQ ID NO: 11) | RMVGTGGYAMDA (SEQ ID NO: 12) |
| MP28132 | GYTFTSN (SEQ ID NO: 2) | YRGDGD (SEQ ID NO: 13) | GDSSGWGPNWFDS (SEQ ID NO: 14) |

TABLE 2

Variable Light Chain Usage + CDRs

Variable Light Chain Usage

| Clone | CDR1 | CDR2 | CDR3 |
|---|---|---|---|
| MP27963 | LASQDIGNYLS (SEQ ID NO: 15) | DVNNLED (SEQ ID NO: 16) | QQYYEYPLT (SEQ ID NO: 17) |
| MP27964 | RVSSSVSYMH (SEQ ID NO: 18) | ETSKLAS (SEQ ID NO: 19) | QQWNFPLT (SEQ ID NO: 20) |
| MP27965 | RASEDIYSNLA (SEQ ID NO: 21) | DANNLAD (SEQ ID NO: 22) | QQYNNYPLT (SEQ ID NO: 23) |
| MP27966 | LASQDIGDYLS (SEQ ID NO: 24) | GATNLED (SEQ ID NO: 25) | HQYYQYPLT (SEQ ID NO: 26) |
| MP27967 | RASQSVSISSVNLMN (SEQ ID NO: 27) | HASNLAS (SEQ ID NO: 28) | QQSRESPWT (SEQ ID NO: 29) |
| MP28132 | RASEDIYSNLA (SEQ ID NO: 21) | DANSLAD (SEQ ID NO: 57) | QQYNNYPLT (SEQ ID NO: 23) |

The CD21-binding domain may comprise a VH which comprises a CDR selected from SEQ ID NO: 4, 6, 9, 12, or 14 or a variant thereof with up to three amino acid mutations (e.g. 1, 2 or 3 mutations).

The CD21-binding domain may comprise a VL which comprises a CDR selected from SEQ ID NO: 17, 20, 23, 26 or 29 or a variant thereof with up to three amino acid mutations (e.g. 1, 2 or 3 mutations).

It may be possible to introduce one or more mutations (substitutions, additions or deletions) into a CDR without negatively affecting CD21-binding activity. The CDR may, for example, have one, two or three amino acid mutations, for example one, two or three amino acid substitutions. Preferably, the amino acid substitutions are conservative substitutions.

Conservative amino acid substitutions may be made on the basis of similarity in polarity, charge, solubility, hydrophobicity, hydrophilicity, and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to Table 3 below. Amino acids in the same block in the second column and preferably in the same line in the third column may be substituted for each other:

TABLE 3

| ALIPHATIC | Non-polar | G A P |
|---|---|---|
| | | I L V |
| | Polar-uncharged | C S T M |
| | | N Q |
| | Polar-charged | D E |
| | | K R |
| AROMATIC | | H F W Y |

The present invention also encompasses homologous substitution (substitution and replacement are both used herein to mean the interchange of an existing amino acid residue, with an alternative residue) i.e. like-for-like substitution such as basic for basic, acidic for acidic, polar for polar etc.

Unless otherwise explicitly stated herein by way of reference to a specific, individual amino acid, amino acids may be substituted using conservative substitutions as recited below.

An aliphatic, non-polar amino acid may be a glycine, alanine, proline, isoleucine, leucine or valine residue.

An aliphatic, polar uncharged amino may be a cysteine, serine, threonine, methionine, asparagine or glutamine residue.

An aliphatic, polar charged amino acid may be an aspartic acid, glutamic acid, lysine or arginine residue.

An aromatic amino acid may be a histidine, phenylalanine, tryptophan or tyrosine residue.

Suitably, a conservative substitution may be made between amino acids in the same line in Table 3.

The CD21-binding domain may comprise six CDRs selected from (i) to (vi) as follows: (i) SEQ ID NOs: 2 to 4 and 15 to 17 or variants thereof with up to three amino acid substitutions in each CDR; (ii) SEQ ID NOs: 2, 5, 6 and 18 to 20 or variants thereof with up to three amino acid substitutions in each CDR; (iii) SEQ ID NOs: 7 to 9 and 21 to 23 or variants thereof with up to three amino acid substitutions in each CDR; (iv) SEQ ID NOs: 7 to 9 and 24 to 26 or variants thereof with up to three amino acid substitutions in each CDR; (v) SEQ ID NOs: 10 to 12 and 27 to 29 or variants thereof with up to three amino acid substitutions in each CDR in each CDR; and (vi) SEQ ID NOs: 2, 13, 14, 21, 57 and 23 or variants thereof with up to three amino acid mutations in each CDR.

The CD21-binding domain may comprise six CDRs of a CD21-binder as shown in Tables 2 and 3.

The C21-binding domain may comprise six CDRs selected from (i) to (vi) as follows: (i) SEQ ID NOs: 2 to 4 and 15 to 17; (ii) SEQ ID NOs: 2, 5, 6 and 18 to 20; (iii) SEQ ID NOs: 7 to 9 and 21 to 23; (iv) SEQ ID NOs: 7 to 9 and 24 to 26; (v) SEQ ID NOs: 10 to 12 and 27 to 29; and (vi) SEQ ID NOs: 2, 13, 14, 21, 57 and 23.

The CD21-binding domain may comprise six CDRs shown as SEQ ID NOs: 2 to 4 and 15 to 17 or variants thereof with up to three amino acid mutations, preferably substitutions, in each CDR. The CD21-binding domain may comprise six CDRs shown as SEQ ID NOs: 2 to 4 and 15 to 17.

The CD21-binding domain may comprise six CDRs shown as SEQ ID NOs: 2, 5, 6 and 18 to 20 or variants thereof with up to three amino acid mutations, preferably substitutions, in each CDR. The CD21-binding domain may comprise six CDRs shown as SEQ ID NOs: 2, 5, 6 and 18 to 20.

The CD21-binding domain may comprise six CDRs shown as SEQ ID NOs: 7 to 9 and 21 to 23 or variants thereof with up to three amino acid mutations, preferably substitutions, in each CDR. The CD21-binding domain may comprise six CDRs shown as SEQ ID NOs: 7 to 9 and 21 to 23.

The CD21-binding domain may comprise six CDRs shown as SEQ ID NOs: 7 to 9 and 24 to 26 or variants thereof with up to three amino acid mutations, preferably substitutions, in each CDR. The CD21-binding domain may comprise six CDRs shown as SEQ ID NOs: 7 to 9 and 24 to 26.

The CD21-binding domain may comprise six CDRs shown as SEQ ID NOs: 10 to 12 and 27 to 29 or variants thereof with up to three amino acid mutations, preferably substitutions, in each CDR. The CD21-binding domain may comprise six CDRs shown as SEQ ID NOs: 10 to 12 and 27 to 29.

The CD21-binding domain may comprise six CDRs shown as SEQ ID NOs: 13, 14, 21, 57 and 23 or variants thereof with up to three amino acid mutations, preferably substitutions, in each CDR. The CD21-binding domain may comprise six CDRs shown as SEQ ID NOs: 2, 13, 14, 21, 57 and 23.

The CD21-binding domain may comprise a variable heavy chain shown as any one of SEQ ID NO: 38-46 or a variant thereof having at least 80% sequence identity thereto.

The CD21-binding domain may comprise a variable light chain shown as any one of SEQ ID NO: 47-55 or a variant thereof having at least 80% sequence identity thereto.

The CD21-binding domain may comprise a variable heavy chain and a variable light chain pair as shown in the table below, or a variant of the corresponding sequence shown as SEQ ID NO: 38-55 having at least 80% sequence identity thereto, such that the variable heavy and light chain pair retains the ability to bind to CD21. Suitably, the variant variable heavy and light chain pair may bind to CD21 at least as well as the corresponding variable heavy and light chain pair in the table. In other words, the variant may specifically bind to CD21 with a binding affinity which is at least equivalent to the binding affinity between the corresponding variable heavy and light chain pair shown below and CD21.

The variant may have at least 80, 85, 90, 95, 98 or 99% sequence identity to any one of SEQ ID NO: 38-55.

| | SEQ ID NO: | Amino Acid Sequence |
|---|---|---|
| 1 | 38 | QVQLQQSGAELVRPGSSVKISCKASGYTETSNEMHWIKQQPGNGLEWIGWISPGDGDT EYNQKENGKATITADESSSTAYIQLSGLTSEDSAVYFCARGDSSGWGPNWEDSWGQGT LVTVSS |
| | 39 | DIQMTQSPSSMSASLGDTVTITCLASQDIGNYLSWYQQKPGKSPKLMIYDVNNLEDGV PSRESGSRSGSNHSLTINSLGYDDEGIYHCQQYYEYPLTEGSGTKLEIKR |
| 2 | 40 | EVHLQQSGAELVKPGSSVKISCKASGYTFTSNFMHWIKQQPGNGLEWIGWIYPGDGDT EYNQKENGKASLTADKSSSTAYMQLSSLTSEDSAVYFCALSGDGYEDYWGQGVMVTVS S |
| | 41 | EIVLTQSPTTMTASPGEKVTITCRVSSSVSYMHWYQQKPDASPKPWIYETSKLASGVP DRFSGSGSGTSYSLTINNMEABDAATYYCQQWNEPLTEGSGTKLEIKR |
| 3 | 42 | VQLQQSGAELVKPGSSVKISCKASGYTFTTNFMHWIKQQPGNGLEWIGWINPGDGNTE YNQKFNVKATLTADKSSSTAYMELGSLTSEDSAVYFCARGDYSGWGPNWFDYWGQGTL VTVSS |

| SEQ ID NO: | Amino Acid Sequence |
|---|---|
| 43 | DIQMTQSPASLSASLGETVTIECRASEDIYSNLAWYQQKPGNSPQLLIHDANNLADGVPSRFSGSGSGTQYSLKINSLQSEDVASYFCQQYNNYPLTFGSGTKLEIKR |
| 4 44 | QVQLQQSGAELVKPGSSVKISCKASGYTFTTNFMHWIKQQPGNGLEWIGWINPGDGNTEYNQKFNVKATLTADKSSSTAYMELGSLISEDSAVYECARGDYSGWGPNWFDYWGQGTLVTVSS |
| 45 | DIQLTQSPSSMSASLGDTVTITCLASQDIGDYLSWYQQKPGKSPKVMVYGATNIEDGVPSRFSGSRSGSDYSLTINSIGYDDEGIYHCHQYYQYPLTEGSGTKLEIKR |
| 5 46 | EVQLQQSGAELGKPGTSVKLSCKVSGYNIRNTYIBWVNQRPGKGLEWIGRIDPANGDTIYAEKFKSKATLTADTSSNTAYMQLSQLKSDDTAIYFCAMRMVGTGGYAMDAWGQGASVTVSS |
| 47 | DIVLTQSPALAVSPGQRATISCRASQSVSISSVNLMNWYQQKPGQQPKLLIYHASNLASGIPTRFSGSGSGTDFTLTIQPVQADDIATYYCQQSRESPWTFGGGTKLELKR |
| 6 48 | VQLQQSGAELVEPGSSVKISCKASGYTFTSNEMHWIRQQPGNGLEWIGWVYRGDGDTEYNQRFNGKATLTADESSSTAYIQLSGLTSEDSAVYFCARGDSSGWGPNWEDSWGQGTLVTVSS |
| 49 | DVQMTQSPASLSASIGETVTIECRASEDIYSNLAWYQQKPGNSPQLLIYDANSLADGVPSRFSGSGSGTQYSLKINSLQSEDVASYFCQQYNNYPLTFGSETRLEIKR |
| 7 50 | QVQLQQSGAQLVKPGSSVKLSCKTSGFTFSSSYISWLKQAPGQSFEWIGNIFAGDGGPNYSQKEKGKATLTVDTSSNTAYMDLSSLISEDSALYFCARPWANWGQGTLVTVSS |
| 51 | EIVITQSPTTTAASPGEKVTITCLASSSASNMFWYQQKSGDSPKLLIYSTSSLASGVPDRFSGSGSGTSYSLTISSMEAEDAATYYCLQRSSYPWTFGGGTKLELKR |
| 8 52 | EVQLVETGGGIVQPGKSLKLTCATSGFTFSTAWMAWVRQSPDKRLEWIARIKDKSKNYATDYVEAVKGRFSISRDDSKSSVYLQMNSLKEEDTATYYCTTGTYRYYEDYWGQGVMVTVSS |
| 53 | EIVLTQSPTTTAASPGEKVTITCLANSSVSNMYWYQQKSGASPKLLIYSTSRLASGVPDRFSGSGSGTSSSLTINTMEAEDAATYYCQQWSSDPPTFGSGTKLELKR |
| 9 54 | VQLQQSGAELAKPGSSVKISCKASGYTFTNYHITWIRQTTGQGLEYVGYINTGSGTTYYNEKEKGKATLTVDKSSSTAFMQLSSLTPDDSAVYYCARLVLHWFAYWGQGTLVTVSS |
| 55 | DIVMTQGALPNPVPSGEVASITCQSSKSLLASNGKTYLNWYLQRPGQSPQLLIYWMSTRASGVSDRESGSGSGTDETLKISSVEAEDVGVYYCQQFLEYPRTFGGGTKLELKR |

The CDRs may be grafted onto the framework of a human antibody or scFv.

The CD21-binding domain may be a scFv. A scFv is a fusion protein of the heavy variable region (VH) and light chain variable region (VL) of an antibody, connected with a short linker peptide of ten to about 25 amino acids. The scFv may be in the orientation VH-VL, i.e. the VH is at the amino-terminus of the CAR molecule and the VL domain is linked to the spacer and, in turn the transmembrane domain and endodomain.

The scFv may comprise a sequence shown as SEQ ID NO: 30-37 or 58 or a variant of any one of SEQ ID NO: 30-37 or 58 having at least 80% sequence identity thereto and retaining the ability to bind to CD21. Suitably, the variant may bind to CD21 at least as well as the corresponding scFv shown as SEQ ID NO: 30-37 or 58. In other words, the variant may specifically bind to CD21 with a binding affinity which is at least equivalent to the binding affinity between the corresponding scFv shown as SEQ ID NO: 30-37 or 58 and CD21.

Binding affinities may be determined using SPR methodologies, for example as described herein.

| SEQ ID NO: | scFv Amino Acid Sequence |
|---|---|
| 58 | QVQLQQSGAELVRPGSSVKISCKASGYTFTSNFMAWIKQQPGNGLEWIGWISPGDGDTRYNQKFNGKATLTADESSSTAYIQLSGLTSEDSAVYFCARGDSSGWGPNWFDSWGQGTLVTVSSGGGGSGGGGSGGGGSDIQMTQSPSSMSASLGDTVTITCLASQDIGNYLSWYQQKPGKSPKLMIYDVNNLEDGVPSRFSGSRSGSNASLTINSLGYDDEGIYHCQQYYEYPLTFGSGTKLEIKR |
| 30 | EVALQQSGAELVKPGSSVKISCKASGYTFTSNFMHWIKQQPGNGLEWIGWIYPGDGTEYNQKFNGKASLTADKSSSTAYMQLSSLTSEDSAVYFCALSGDGYFDYWGQGVMVTVSSGGGGSGGGGSGGGGSEIVLTQSPTTMTASPGEKVTITCRVSSSVSYMHWYQQKPDASPKPWIYETSKLASGVPDRFSGSGSGTSYSLTINNMEAEDAATYYCQQWNFPLTFGSGTKLEIKR |

-continued

| SEQ ID NO: | scFv Amino Acid Sequence |
|---|---|
| 31 | QVQLQQSGAELVKPGSSVKISCKASGYTFTTNFMHWIKQQPGNGLEWIGWINPGDGNTEYNQ<br>KFNVKATLTADKSSSTAYMELGSLTSEDSAVYFCARGDYSGWGPNWFDYWGQGTLVTVSSDG<br>GGSGGGGSGGGGSDIQMTQSPASLSASLGETVTIECRASEDIYSNLAWYQQKPGNSPQLLIB<br>DANNLADGVPSRFSGSGSGTQYSLKINSLQSEDVASYFCQQYNNYPLTFGSGTKLEIKR |
| 32 | QVQLQQSGAELVKPGSSVKISCKASGYTFTTNFMAWIKQQPGNGLEWIGWINPGDGNTEYNQ<br>KFNVKATLTADKSSSTAYMELGSLTSEDSAVYFCARGDYSGWGPNWFDYWGQGTLVTVSSGG<br>GGSGGGGSGGGGSDIQLTQSPSSMSASLGDTVTITCLASQDIGDYLSWYQQKPGKSPKVMVY<br>GATNLEDGVPSRFSGSRSGSDYSLTINSLGYDDEGIYHCHQYYQYPLTFGSGTKLEIKR |
| 33 | EVQLQQSGAELGKPGTSVKLSCKVSGYNIRNTYIHWVNQRPGLEWIGRIDPANGDTIYAE<br>KFKSKATLTADTSSNTAYMQLSQLKSDDTAIYFCAMRMVGTGQGASVTVSSGGG<br>GSGGGGGGGGGSDIVLTQSPALAVSPGQRATISCRASQSVSISSVNLMNWYQQKPGQQPKLL<br>IYHASNLASGIPTRFSGSGSGTDFTLTIDPVQADDIATYYCQQSRESPWTFGGGTKLELKR |
| 34 | QVQLQQSGAELVEPGSSVKISCKASGYTFTSNFMHWIRQQPGNGLEWIGWVYRGDGDTEYNQ<br>RFNGKATLTADESSSTAYIQLSGLISEDSAVYFCARGDSSGWGPNWFDSWGQGTLVTVSSGG<br>GGSGGGGSGGGGSDVQMTQSPASLSASIGETVTIECRASEDIYSNLAWYQQKPGNSPQLLIY<br>DANSLADGVPSRFSGSGSGTQYSLKINSLQSEDVASYFCQQYNNYPLTFGSETRLEIKR |
| 35 | QVQIQQSGAQLVKPGSSVKLSCKTSGFTFSSSYISWLKQAPGQSFEWIGNIFAGDGGPNYSQ<br>KFKGKATLIVDTSSNTAYMDLSSLTSEDSALYFCARPWANWGQGTLVTVSSGGGGGGGGSG<br>GGGSEIVLTQSPTTTAASPGEKVTITCLASSSASNMFWYQQKSGDSPKLLIYSTSSLASGVP<br>DRFSGSGSGTSYSLTISSMEAEDAATYYCLQRSSYPWTFGGGTKLELKR |
| 36 | EVQLVETGGGLVQPGKSLKLTCATSGFTFSTAWMHWVRQSPDKRLEWIARIKDKSKNYATDY<br>VEAVKGRFSISRDDSKSSVYLQMNSLKEEDTATYYCTTGTYRYYFDYWGQGVMVTVSSGGGG<br>SGGGGSGGGGSEIVLTQSPTTTAASPGEKVTITCLANSSVSNMYWYQQKSGASPKLLIYSTS<br>RLASGVPDRFSGSGSGTSSSLTINTMEAEDAATYYCQQWSSDPPTFGSGTKLELKR |
| 37 | QVQLQQSGAELAKPGSSVKISCKASGYTFTNYBITWIKQTTGQGLEYVGYINTGSGTTYYNE<br>KFKGKATLTVDKSSSTAFMQLSSLIPDDSAVYYCARLVLAWFAYWGQGTLVTVSSGGGGSGG<br>GGSGGGGSDIVMTQGALPNPVPSGEVASITCQSSKSLLASNGKTYLNWYLQRPGQSPQLLIY<br>WMSTRASGVSDRFSGSGSGTDFTLKISSVEAEDVGVYYCQQFLEYPRTFGGGTKLELKR |

The scFv may comprise a sequence shown as SEQ ID NO: 58 or a variant having at least 80, 85, 90, 95, 98 or 99% sequence identity to SEQ ID NO: 58 and retaining the ability to bind to CD21.

The scFv may comprise a sequence shown as SEQ ID NO: 30 or a variant having at least 80, 85, 90, 95, 98 or 99% sequence identity to SEQ ID NO: 30 and retaining the ability to bind to CD21.

The scFv may comprise a sequence shown as SEQ ID NO: 31 or a variant having at least 80, 85, 90, 95, 98 or 99% sequence identity to SEQ ID NO: 31 and retaining the ability to bind to CD21.

The scFv may comprise a sequence shown as SEQ ID NO: 32 or a variant having at least 80, 85, 90, 95, 98 or 99% sequence identity to SEQ ID NO: 32 and retaining the ability to bind to CD21.

The scFv may comprise a sequence shown as SEQ ID NO: 33 or a variant having at least 80, 85, 90, 95, 98 or 99% sequence identity to SEQ ID NO: 33 and retaining the ability to bind to CD21.

The scFv may comprise a sequence shown as SEQ ID NO: 34 or a variant having at least 80, 85, 90, 95, 98 or 99% sequence identity to SEQ ID NO: 34 and retaining the ability to bind to CD21.

The scFv may comprise a sequence shown as SEQ ID NO: 35 or a variant having at least 80, 85, 90, 95, 98 or 99% sequence identity to SEQ ID NO: 35 and retaining the ability to bind to CD21.

The scFv may comprise a sequence shown as SEQ ID NO: 36 or a variant having at least 80, 85, 90, 95, 98 or 99% sequence identity to SEQ ID NO: 36 and retaining the ability to bind to CD21.

The scFv may comprise a sequence shown as SEQ ID NO: 37 or a variant having at least 80, 85, 90, 95, 98 or 99% sequence identity to SEQ ID NO: 37 and retaining the ability to bind to CD21.

The "GGGGSGGGGSGGGGS" (SEQ ID NO: 56) linker sequence of any one of the scFVs shown as SEQ ID NO: 29-37 may be replaced with a suitable, alternative linker sequence.

Transmembrane Domain

The transmembrane domain is the sequence of a classical CAR that spans the membrane. The transmembrane domain may be any protein structure which is thermodynamically stable in a membrane. This is typically an alpha helix comprising of several hydrophobic residues. The transmembrane domain of any transmembrane protein can be used to supply a transmembrane portion. The presence and span of a transmembrane domain of a protein can be determined by those skilled in the art using the TMHMM algorithm (http://www.cbs.dtu.dk/services/TMHMM-2.0/). Further, given that the transmembrane domain of a protein is a relatively simple structure, i.e a polypeptide sequence predicted to form a hydrophobic alpha helix of sufficient length to span the membrane, an artificially designed TM domain may also be used (U.S. Pat. No. 7,052,906 B1 describes transmembrane components).

The transmembrane domain of the CAR may comprise a hydrophobic alpha helix. The transmembrane domain may be derived from CD28, which gives good receptor stability. The transmembrane domain may comprise the sequence shown as SEQ ID NO: 24 or a variant thereof having at least 80% sequence identity.

SEQ ID NO. 59
FWVLVVVGGVLACYSLLVTVAFIIFWV

The variant may have at least 80, 85, 90, 95, 98 or 99% sequence identity with SEQ ID NO: 59, provided that the variant sequence retains the capacity to traverse the membrane.

Signal Peptide

The CAR may comprise a signal peptide so that when it is expressed in a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch or amino acids that is recognized and cleaved by signal peptidase. Signal peptidase may cleave either during or after completion of translocation to generate a free signal peptide and a mature protein. The free signal peptides are then digested by specific proteases.

Spacer Domain

The CAR may comprise a spacer sequence to connect the antigen-binding domain with the transmembrane domain. A flexible spacer allows the antigen-binding domain to orient in different directions to facilitate binding.

The spacer sequence may, for example, comprise an IgG1 Fc region, an IgG1 hinge or a human CD8 stalk or the mouse CD8 stalk. The spacer may alternatively comprise an alternative linker sequence which has similar length and/or domain spacing properties as an IgG1 Fc region, an IgG1 hinge or a CD8 stalk. A human IgG1 spacer may be altered to remove Fc binding motifs.

Intracellular Domain

The intracellular domain is the signal-transmission portion of a classical CAR.

The most commonly used signalling domain component is that of CD3-zeta endodomain, which contains 3 ITAMs. This transmits an activation signal to the T cell after antigen is bound. CD3-zeta may not provide a fully competent activation signal and additional co-stimulatory signalling may be needed. For example, chimeric CD28 and OX40 can be used with CD3-Zeta to transmit a proliferative/survival signal, or all three can be used together (illustrated in FIG. 1B).

The intracellular signalling domain may be or comprise a T cell signalling domain.

The intracellular signalling domain may comprise one or more immunoreceptor tyrosine-based activation motifs (ITAMs). An ITAM is a conserved sequence of four amino acids that is repeated twice in the cytoplasmic tails of certain cell surface proteins of the immune system. The motif contains a tyrosine separated from a leucine or isoleucine by any two other amino acids, giving the signature YxxL/1. Two of these signatures are typically separated by between 6 and 8 amino acids in the tail of the molecule (YxxL/Ix$_{(6-8)}$YxxL/I).

ITAMs are important for signal transduction in immune cells. Hence, they are found in the tails of important cell signalling molecules such as the CD3 and ζ-chains of the T cell receptor complex, the CD79 alpha and beta chains of the B cell receptor complex, and certain Fc receptors. The tyrosine residues within these motifs become phosphorylated following interaction of the receptor molecules with their ligands and form docking sites for other proteins involved in the signalling pathways of the cell.

The intracellular signalling domain component may comprise, consist essentially of, or consist of the CD3-ζ endodomain, which contains three ITAMs. Classically, the CD3-ζ endodomain transmits an activation signal to the T cell after antigen is bound. However, in the context of the present invention, the CD3-ζ endodomain transmits an activation signal to the T cell after the MHC/peptide complex comprising the engineered B2M binds to a TCR on a different T cell.

The intracellular signalling domain may comprise additional co-stimulatory signalling. For example, 4-1BB (also known as CD137) can be used with CD3-ζ, or CD28 and OX40 can be used with CD3-ζ to transmit a proliferative/survival signal.

Accordingly, intracellular signalling domain may comprise the CD3-ζ endodomain alone, the CD3-ζ endodomain in combination with one or more co-stimulatory domains selected from 4-1BB, CD28 or OX40 endodomain, and/or a combination of some or all of 4-1BB, CD28 or OX40.

The endodomain may comprise one or more of the following: an ICOS endodomain, a CD2 endodomain, a CD27 endodomain, or a CD40 endodomain.

The endomain may comprise the sequence shown as SEQ ID NO: 60 to 63 or a variant thereof having at least 80, 85, 90, 95, 98 or 99% sequence identity, provided that the variant sequence retains the capacity to transmit an activating signal to the cell.

As used throughout this disclosure, the percentage identity between two polypeptide sequences may be readily determined by programs such as BLAST, which is freely available at http://blast.ncbi.nlm.nih.gov. Suitably, the percentage identity is determined across the entirety of the reference and/or the query sequence.

SEQ ID NO: 60 - CD3-ζ endodomain
RVKFSRSADAPAYQQGQNQLYNELNLGRREEYDVLDKRRGRDPEMGGKP
RRKNPQEGLYNELQKDKMAEAYSEIGMKGERRRGKGHDGLYQGLSTATK
DTYDALHMQALPPR SEQ ID NO: 61 - 4-1BB and CD3-ζ endodomains
MGNSCYNIVATLLLVENFERTRSLQDPCSNCPAGTFCDNNRNQICSPCP
PNSESSAGGQRTCDICRQCKGVFRTRKECSSTSNAECDCTPGFHCLGAG
CSMCEQDCKQGQELTKKGCKDCCFGTFNDQKRGICRPWTNCSLDGKSVL
VNGTKERDVVCGPSPADLSPGASSVTPPAPAREPGHSPQIISFFLALIS
TALLFLLFELTLRFSVVKRGRKKLLYIFKQPEMRPVQTTQEEDGCCRFP
EEEEGGCELRVKFSRSADAPAYQQGQNQLYNELNLGRREEYDVLDKRRG
RDPEMGGKPQRRKNPQEGLYNELQKDKMAEAYSEIGMKGERRRGKGHDG
LYQGLSTATKDTYDALHMQALPPR SEQ ID NO: 62 - CD28 and CD3-ζ endodomains
SKRSRLLHSDYMNMTPRRPGPTRKHYQPYAPPRDFAAYRSRVKFSRSAD
APAYQQGQNQLYNELNLGRREEYDVLDKRRGRDPEMGGKPRRKNPQEGL
YNELQKDKMAEAYSEIGMKGERRRGKGHDGLYQGLSTATKDTYDALHMQ
ALPPR SEQ ID NO: 63 - CD28, OX40 and CD3-ζ endodomains
SKRSRLLHSDYMNMTPRRPGPTRKHYQPYAPPRDFAAYRSRDQRLPPDA
HKPPGGGSERTPIQEEQADAHSTLAKIRVKFSRSADAPAYQQGQNQLYN
ELNLGRREEYDVLDKRRGRDPEMGGKPRRKNPQEGLYNELQKDKMAEAY
SEIGMKGERRRGKGHDGLYQGLSTATKDTYDALHMQALPPR Suitably, the CAR may have the general format: antigen-binding domain—TCR element.

As used herein "TCR element" means a domain or portion thereof of a component of the TCR receptor complex. The TCR element may comprise (e.g. have) an extracellular domain and/or a transmembrane domain and/or an intracellular domain e.g. intracellular signalling domain of a TCR element.

The TCR element may selected from TCR alpha chain, TCR beta chain, a CD3 epsilon chain, a CD3 gamma chain, a CD3 delta chain, CD3 epsilon chain.

Suitably, the TCR element may comprise the extracellular domain of the TCR alpha chain, TCR beta chain, a CD3 epsilon chain, a CD3 gamma chain, a CD3 delta chain, or CD3 epsilon chain.

Suitably, the TCR element may comprise the transmembrane domain of the TCR alpha chain, TCR beta chain, a CD3 epsilon chain, a CD3 gamma chain, a CD3 delta chain, or CD3 epsilon chain.

Suitably, the TCR element may comprise the intracellular domain of the TCR alpha chain, TCR beta chain, a CD3 epsilon chain, a CD3 gamma chain, a CD3 delta chain, or CD3 epsilon chain.

Suitably, the TCR element may comprise the TCR alpha chain, TCR beta chain, a CD3 epsilon chain, a CD3 gamma chain, a CD3 delta chain, or CD3 epsilon chain.

Polynucleotide

As used herein, the terms "polynucleotide", "nucleotide", "nucleic acid sequence" and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described herein to reflect the codon usage of any particular host organism in which the polypeptides are to be expressed. Suitably, the polynucleotides of the present invention are codon optimised to enable expression in a mammalian cell, in particular an immune effector cell as described herein.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art.

Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

Vector

The present invention also provides a vector, which comprises one or more nucleic acid sequence(s) of the invention. Such a vector may be used to introduce the nucleic acid sequence(s) or construct(s) into a host cell so that it expresses a CAR of the present invention.

The vector may, for example, be a plasmid or a viral vector, such as a retroviral vector or a lentiviral vector, or a transposon based vector or synthetic mRNA.

The vector may be capable of transfecting or transducing a cell.

Cell

The cell of the present invention may be an immune effector cell, such as a T-cell, a natural killer (NK) cell or a cytokine induced killer cell.

The T cell may be an alpha-beta T cell or a gamma-delta T cell.

The cell may be derived from a patient's own peripheral blood (1st party), or in the setting of a haematopoietic stem cell transplant from donor peripheral blood (2nd party), or peripheral blood from an unconnected donor (3rd party). T or NK cells, for example, may be activated and/or expanded prior to being transduced with nucleic acid molecule(s) encoding the polypeptides of the invention, for example by treatment with an anti-CD3 monoclonal antibody.

Alternatively, the cell may be derived from ex vivo differentiation of inducible progenitor cells or embryonic progenitor cells to T cells. Alternatively, an immortalized T-cell line which retains its lytic function may be used.

The cell may be a haematopoietic stem cell (HSC). HSCs can be obtained for transplant from the bone marrow of a suitably matched donor, by leukopheresis of peripheral blood after mobilization by administration of pharmacological doses of cytokines such as G-CSF [peripheral blood stem cells (PBSCs)], or from the umbilical cord blood (UCB) collected from the placenta after delivery. The marrow, PBSCs, or UCB may be transplanted without processing, or the HSCs may be enriched by immune selection with a monoclonal antibody to the CD34 surface antigen.

Pharmaceutical Composition

The present invention also relates to a pharmaceutical composition containing a cell, a nucleic acid construct, a first nucleic acid sequence and a second nucleic acid sequence; a vector or a first and a second vector of the present invention. In particular, the invention relates to a pharmaceutical composition comprising a cell according to the present invention.

The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The present invention provides a method for treating and/or preventing a disease which comprises the step of administering a cell, a polynucleotide; or a vector of the present invention (for example in a pharmaceutical composition as described above) to a subject.

Suitably, the present methods for treating and/or preventing a disease may comprise administering a cell of the invention (for example in a pharmaceutical composition as described above) to a subject.

A method for treating a disease relates to the therapeutic use of the cells of the present invention. In this respect, the cells may be administered to a subject having an existing disease or condition in order to lessen, reduce or improve at least one symptom associated with the disease and/or to slow down, reduce or block the progression of the disease.

The method for preventing a disease relates to the prophylactic use of the cells of the present invention. In this respect, the cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The method may involve the steps of:
  (i) isolating a cell-containing sample;
  (ii) transducing or transfecting such cells with a polynucleotide or vector provided by the present invention;
  (iii) administering the cells from (ii) to a subject.

The present invention provides a cell, a nucleic acid construct, a first nucleic acid sequence and a second nucleic acid sequence, a vector, or a first and a second vector of the present invention for use in treating and/or preventing a disease. In particular the present invention provides a cell of the present invention for use in treating and/or preventing a disease The invention also relates to the use of a cell, a polynucleotide or a vector of the present invention in the manufacture of a medicament for the treatment and/or prevention of a disease. In particular, the invention relates to the use of a cell in the manufacture of a medicament for the treatment and/or prevention of a disease The disease to be treated and/or prevented by the method of the present invention may be cancer. In particular, the disease may be a cancer comprising tumour cells which express CD21.

Suitably, the disease may be T-cell acute lymphoblastic leukaemia or a B-cell leukaemia or lymphoma.

Suitably, the disease may be T-cell acute lymphoblastic leukaemia.

Suitably, the disease may be a B-cell leukaemia or lymphoma. For example, the disease may be B-cell chronic lymphocytic leukaemia/small lymphocytic lymphoma, Acute lymphoblastic leukaemia, mature B-cell type, B-cell prolymphocytic leukaemia, Precursor B lymphoblastic leukaemia, Hairy cell leukaemia, Diffuse large B-cell lymphoma (DLBCL), Follicular lymphoma, Marginal zone B-cell lymphoma (MZL) or Mucosa-Associated Lymphatic Tissue lymphoma (MALT), Small lymphocytic lymphoma, Mantle cell lymphoma (MCL), Burkitt's lymphoma, Lymphoplasmacytic lymphoma, Nodal marginal zone B cell lymphoma (NMZL), Splenic marginal zone lymphoma (SMZL), Intravascular large B-cell lymphoma, Primary effusion lymphoma, Lymphomatoid granulomatosis, Primary central nervous system lymphoma, ALK-positive large B-cell lymphoma or Plasmablastic lymphoma.

Combination Therapy

The present invention further provides a method of treating and/or preventing a disease which comprises the step of administering a cell, a polynucleotide; or a vector of the present invention (for example in a pharmaceutical composition as described above) in combination with a NOTCH activating agent to a subject.

The disease may be any disease as described herein.

The Notch protein spans the cell membrane, with part of it inside and part outside. Ligand proteins binding to the extracellular domain induce proteolytic cleavage and release of the intracellular domain, which enters the cell nucleus to modify gene expression. Once the notch extracellular domain interacts with a ligand, an ADAM-family metalloprotease called ADAM10, cleaves the notch protein just outside the membrane. This releases the extracellular portion of notch (NECD), which continues to interact with the ligand. The ligand plus the notch extracellular domain is then endocytosed by the ligand-expressing cell. There may be signalling effects in the ligand-expressing cell after endocytosis. After this first cleavage, an enzyme called γ-secretase (which is implicated in Alzheimer's disease) cleaves the remaining part of the notch protein just inside the inner leaflet of the cell membrane of the notch-expressing cell. This releases the intracellular domain of the notch protein (NICD), which then moves to the nucleus, where it can regulate gene expression by activating the transcription factor CSL.

The NOTCH pathway is activated by translocation or mutation (of Notch1 and/or FBXW7) in ~80% of T-ALL cases (see Van Vlierberghe, P. & Ferrando, A.; J. Clin. Invest. 122, 3398-3406 (2012)).

NOTCH activation was associated with upregulation of CD21, suggesting that CD21 is a downstream target of NOTCH. Furthermore, incubation of NOTCH-mutated T-ALL cell lines with the dual PI3K/mTOR kinase inhibitor P1103 led to feedback activation of NOTCH signalling and consequently CD21 expression, in a manner that could be blocked by concomitant NOTCH inhibition (Shepherd, C. et al. Leukemia 27, 650-660 (2013)).

The present inventors have determined that NOTCH mutated and unmutated cell lines incubated with multiple agents which block components of the PI3K/AKT/mTOR pathway results in significant CD21 upregulation in NOTCH mutated T-ALL cell lines only, and loss of CD21 protein expression upon incubation with a gamma-secretase inhibitor, which inhibits NOTCH.

Suitably, the disease may be T-cell acute lymphoblastic leukaemia or a B-cell leukaemia or lymphoma. In particular, the disease may be T-cell acute lymphoblastic leukaemia.

Suitably, the disease may be a cancer in which the tumour cells comprise a mutation which results in activation of the NOTCH pathway. In other words, the cancer may be a NOTCH+ tumour. For example, the tumour cells may comprise a mutation, such as a translocation, substitution, deletion or insertion which results in activation or increased expression of e.g. Notch1 and/or inactivation of FBXW7. The mutation may be a t(7;9)(q34;q34.3) translocation.

Methods for identifying such mutations are well known in the art and include, for example, next-generation sequencing technology such as Solexa and SOLiD platforms. Mutations which result in the activation of NOTCH may be determined by identifying a translocation using metaphase spread and FISH techniques, sequencing Notch gene and determining for upregulation of genes controlled by NOTCH. An illustrative human Notch1 amino acid sequence is provided by UniProt Accession Number P46531. An illustrative human FBXW7 amino acid sequence is provided by UniProt Accession Number Q969H0. A summary of previously identified NOTCH activating mutations and suitable methods for identifying such mutations is provided in Van Vlierberghe, P. & Ferrando, A (as above).

Suitably, the cancer may be a T-cell acute lymphoblastic leukaemia in which tumour cells comprise a mutation which results in activation of the NOTCH pathway.

Accordingly, and without wishing to be bound by theory, the present inventors consider that co-administration of a CD21 CAR-based therapy with an agent that increases NOTCH signalling will improve the efficacy of the CD21 CAR by increasing the level and/or density of CD21 expression on target tumour cells.

"A NOTCH activating agent" is intended to encompass any agent which induces and/or upregulates NOTCH signalling and is suitable for use in a pharmaceutical composition.

For example, suitable NOTCH activating agents may be determined using a reporter assay in a cell line. Suitable reporter assays are known in the art, e.g. as described by Pinchot et al. (Cancer. 2011 Apr. 1; 117(7): 1386-1398; hereby incorporated by reference) or by determining an upregulation of NOTCH regulated gene expression following treatment with the agent. Upregulation of NOTCH regulated gene expression may be determined using commercially available kits and assays (e.g. as provided by Qiagen—RT² Profiler™ PCR Array Human Notch Signalling Pathway).

Suitably, NOTCH activating agent increases CD21 expression in a target cell. Increased CD21 expression may be determined using methods which are known in the art, for example northern blotting, serial analysis of gene expression (SAGE) or quantitative polymerase chain reaction (qPCR). Protein levels in a population of cells may be measured by techniques such as flow cytometry, high-performance liquid chromatography (HPLC), liquid chromatography-mass spectrometry (LC/MS), immunohistochemistry, Western blotting or enzyme-linked immunosorbent assay (ELISA).

For example, the agent may be capable of inhibiting the PI3K/AKT/mTOR pathway.

Suitably, the agent may be a PI3K inhibitor, an AKT inhibitor, a mTOR inhibitor or a combination inhibitor (e.g. an agent which inhibits at least two of PI3K, AKT and mTOR).

The agent may be an allosteric, kinase or dual inhibitor of PI3K, AKT and/or mTOR. The inhibitor may be a dual inhibitor of both PI3K and mTOR.

Suitably, the agent may be a small molecule.

An illustrative list of PI3K inhibitors includes, but is not limited to, pictilisib, idelalisib, buparlisib, ZSTK474, alpelisib, AZD6482, duvelisib, copanlisib, taselisib, serabelisib, GDC0326, umbralisib, AZD8835, nemiralisib, AZD8186, pilaralisib, PX866, MLN1117 and IP1549.

An illustrative list of dual PI3K/mTOR inhibitor includes, but is not limited to, dactolisib (BEZ235), PI103, voxtalisib, omipalisib, PF04691502, apitolisib, GSK1059615, gedatolisib, GDC0084, voxtalisib, SF1126, and PQR309.

An illustrative list of allosteric mTOR inhibitors includes, but is not limited to, sirolimus/rapamycin, everolimus, temsirolimus, and ridaforolimus.

An illustrative list of mTOR kinase inhibitors includes, but is not limited to, AZD8055, KU0063794, Torkinib, sapanisertib, Torin1, Torin2, OSI-027, WYE-354, WYE-132, WYE-687, vistusertib, WAY-600, GDC0349, XL388, MHY1485, CZ415, CC-223, and PP242.

An illustrative list of allosteric/kinase dual mTOR inhibitors includes, but is not limited to, Rapalink-1, Rapalink-2, and Rapalink-3.

An illustrative list of AKT inhibitors includes but is not limited to MK2206, Perifosine, GCK690693, ipatasertib, AZD5363, AT7867, CCT128930, A-674563, PHT-427, afurusertib, AT13148, uprosertib, miransertib, ARQ751, BAY1125976, GSK2141795, LY2780301, and tricribine.

As used herein, 'in combination' means that the cell, polynucleotide; or vector of the present invention (for example in a pharmaceutical composition as described above) may be used simultaneously, sequentially or separately with an agent which increases NOTCH signalling.

Method of Making a Cell

CAR-expressing cells of the present invention may be generated by introducing DNA or RNA coding for the CAR of the present invention.

The cell of the invention may be made by:
(i) isolation of a cell-containing sample from a subject or one of the other sources listed above; and
(ii) transduction or transfection of the cells with one or more a polynucleotide(s) or nucleic acid construct as defined above in vitro or ex vivo.

The cells may then by purified, for example, selected on the basis of expression of the antigen-binding domain of the antigen-binding polypeptide.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The publications discussed herein are provided solely for their disclosure prior to the filing date of the present application. Nothing herein is to be construed as an admission that such publications constitute prior art to the claims appended hereto.

The invention will now be further described by way of Examples, which are meant to serve to assist one of ordinary skill in the art in carrying out the invention and are not intended in any way to limit the scope of the invention.

EXAMPLES

Example 1—CD21 is a Potential Target for T-ALL

Figure 2:
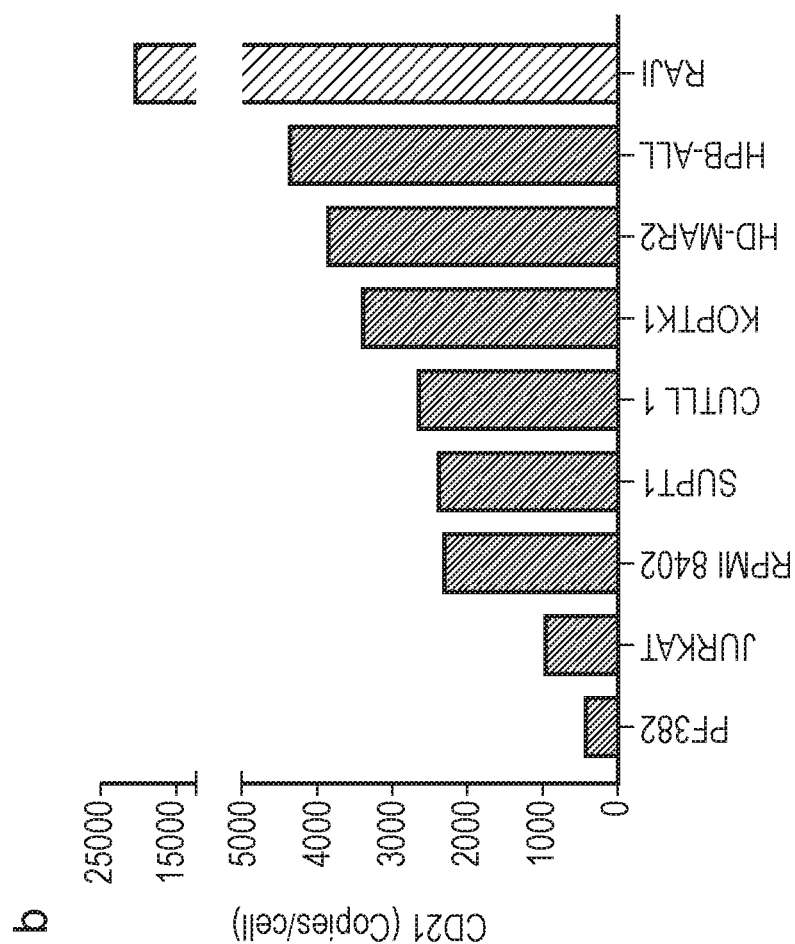
FIG. 2—CD21 is expressed on T-ALL cell lines and primary samples. (a) Proportion of T-ALL cell lines which were CD21+ or CD21− (b) Quantification of surface copies of CD21 on T-ALL cell lines by flow cytometry. Grey=Raji, B-lymphoma line. (c) CD21 expression by microarray in normal/T-ALL blood/marrow, data MILE 2004 database. (d) CD21 expression 30 in 6 patients with T-ALL. 4/6 samples=CD21+ (highlighted in red, panels 3-6). CD7=pan-T marker. (e) Primary T-ALL samples were engrafted in NSG mice by intravenous injection. Flow cytometry plots demonstrate CD21 expression in blast cells isolated from spleens harvested from injected animals.
Figure 2:
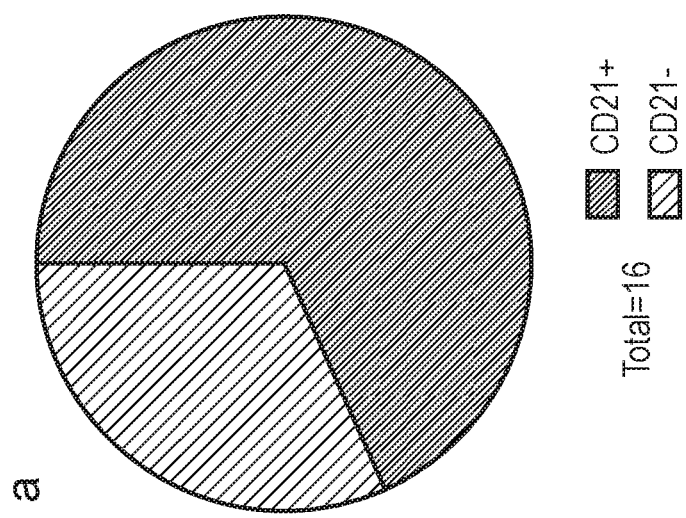
Figure 2:
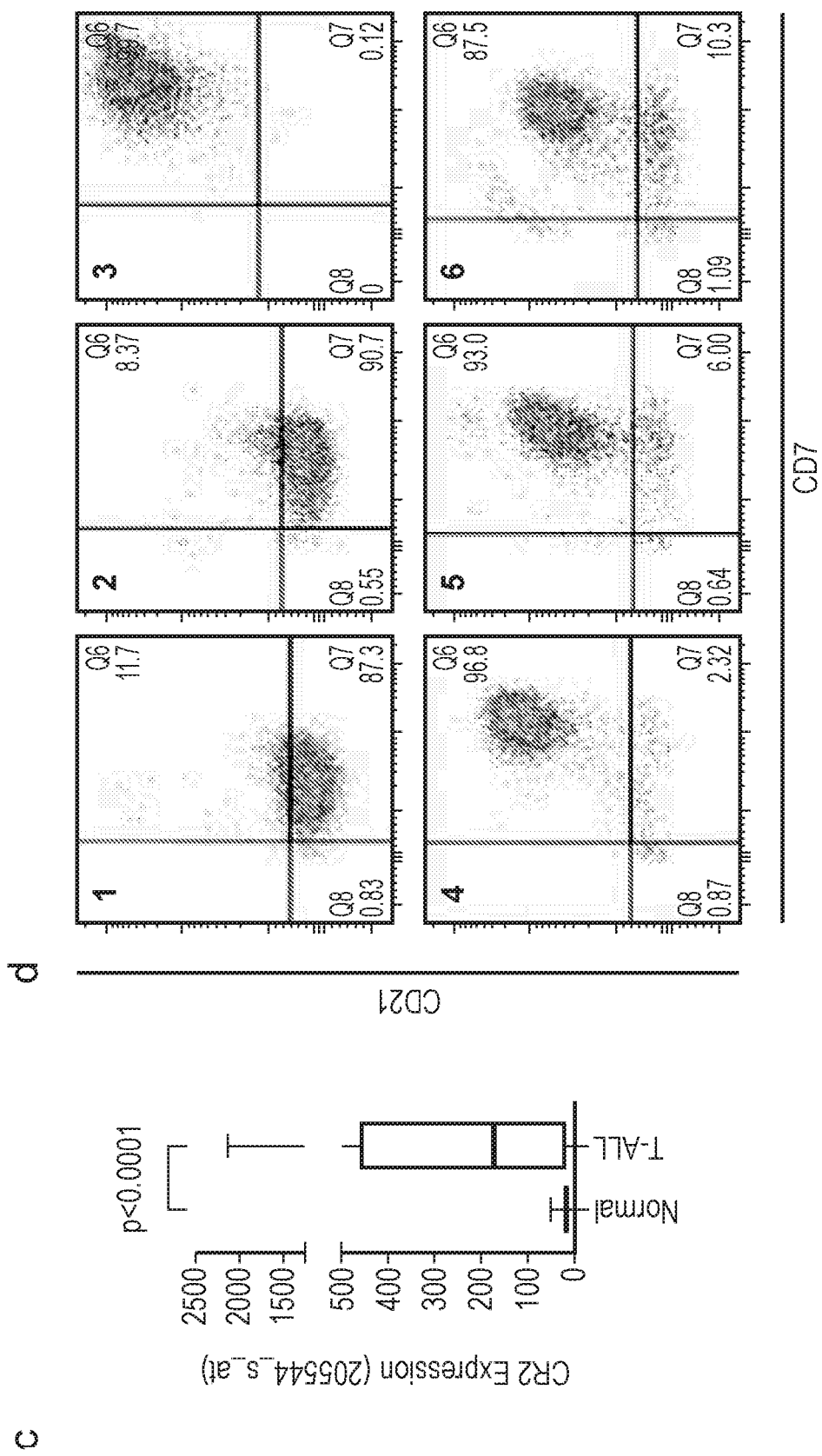
Figure 2:
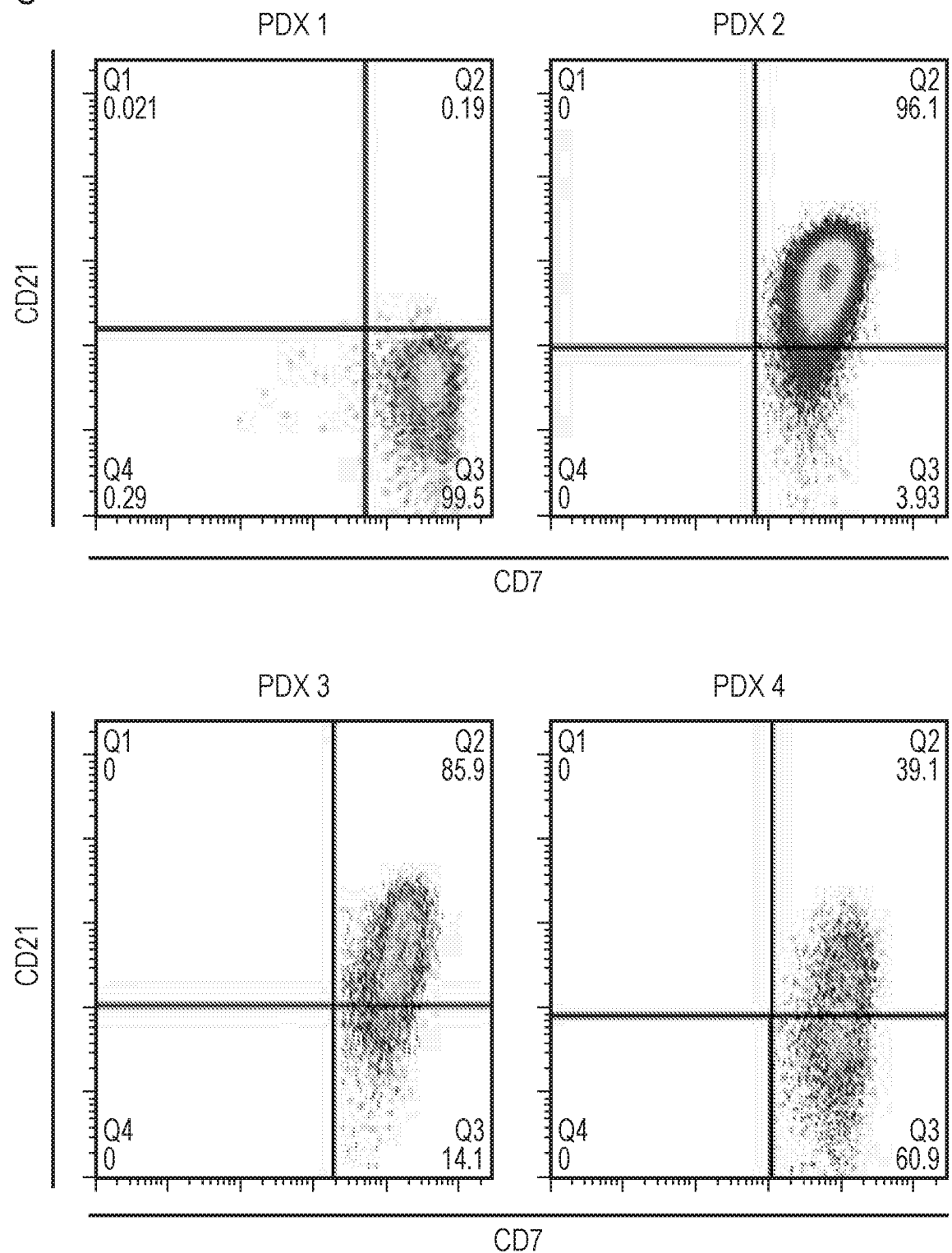

Flow cytometry data demonstrated that CD21 is expressed in ~70% (11/16) of T-ALL cell lines with a median surface copy number of 2545/cell in positive lines. In addition, interrogation of publicly available gene-expression data show that CD21 is upregulated in primary T-ALL. Analysis of CD21 expression by flow cytometry in diagnostic specimens from 22 primary T-ALL cases and showed that 15 (68%) were CD21-positive (FIG. 2D).

Example 2—CD21 is not Expressed on Normal Non-Lymphoid Tissues

Figure 3A:
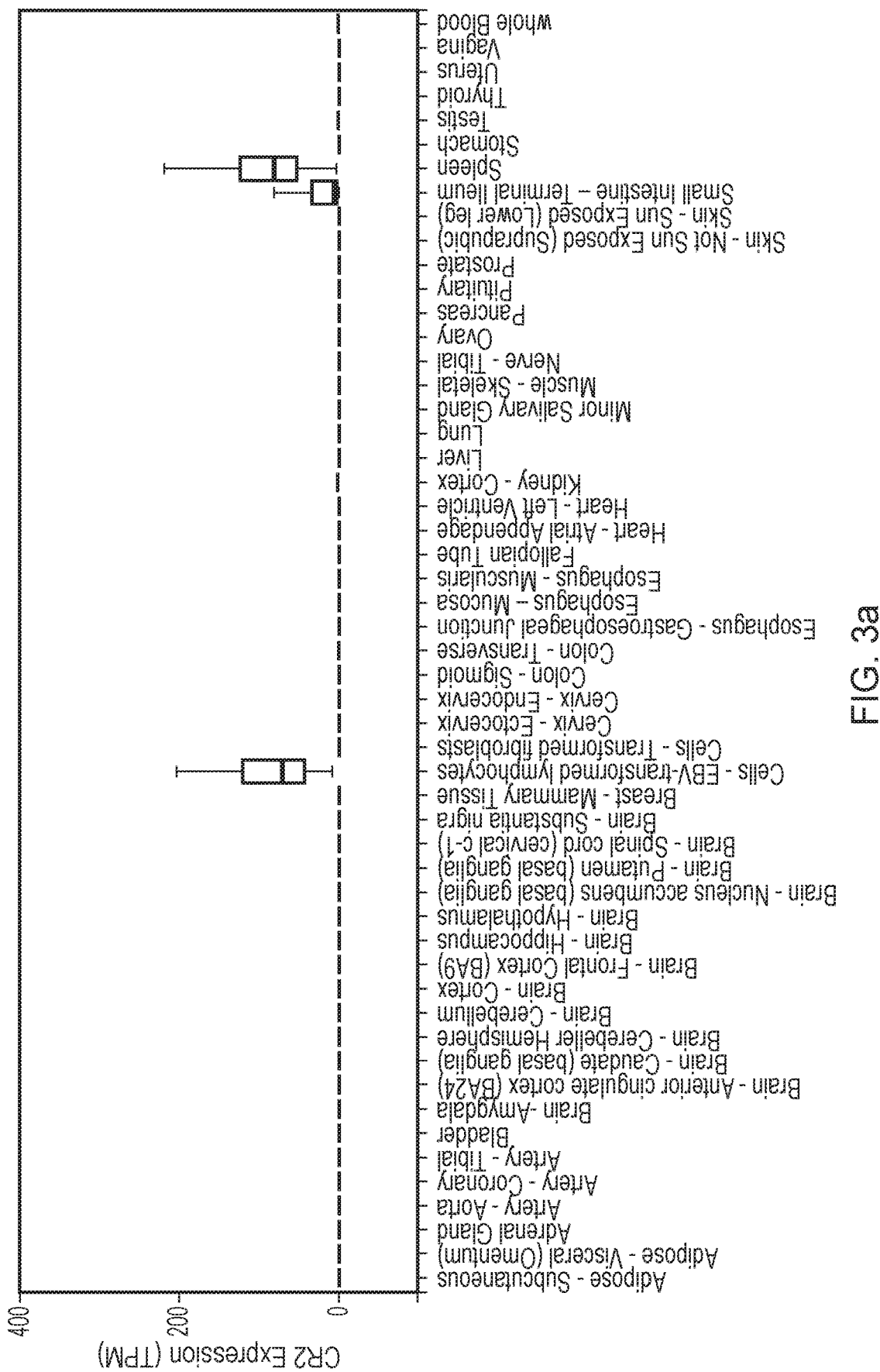
FIG. 3—CD21 expression in normal tissues. (a) RNA-seq expression data for CR2/CD21 from a compendium of normal tissues. Data from GTEx (http://www.gtexportal.org/) (b) Expression of CD21 on peripheral B- and T-cells. Data was obtained by flow cytometry of peripheral blood. (n=11 healthy donors).

CD21 is primarily described on the surface of B cells and follicular dendritic cells (FDCs) where its role as a member of the B cell co-receptor complex binding C3d and as the receptor for EBV is well established. In addition to B-cells, CD21 has also historically been reported to be expressed on about 10% of normal thymocytes, where its function is unknown. RNA expression data across a panel of normal tissues showed a restricted pattern of CD21 expression confined to B-lymphocytes, spleen and terminal ileum (FIG. 3A).

Figure 3B:
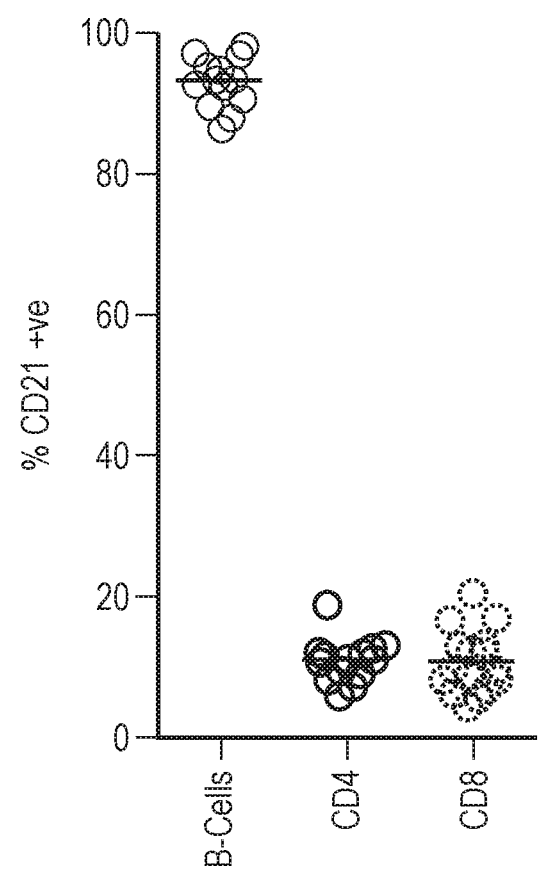

Peripheral blood subset analysis of 11 healthy donors has shown restricted expression of CD21 in cells other than B-lymphocytes, with expression only on <10% of αβ T-cells (FIG. 3B), which was not affected by T-cell stimulation. No expression on erythroid or myeloid compartments was seen in blood or in bone marrow from patients with T-ALL.

Example 3—Binder Discovery for CD21

Figure 4:
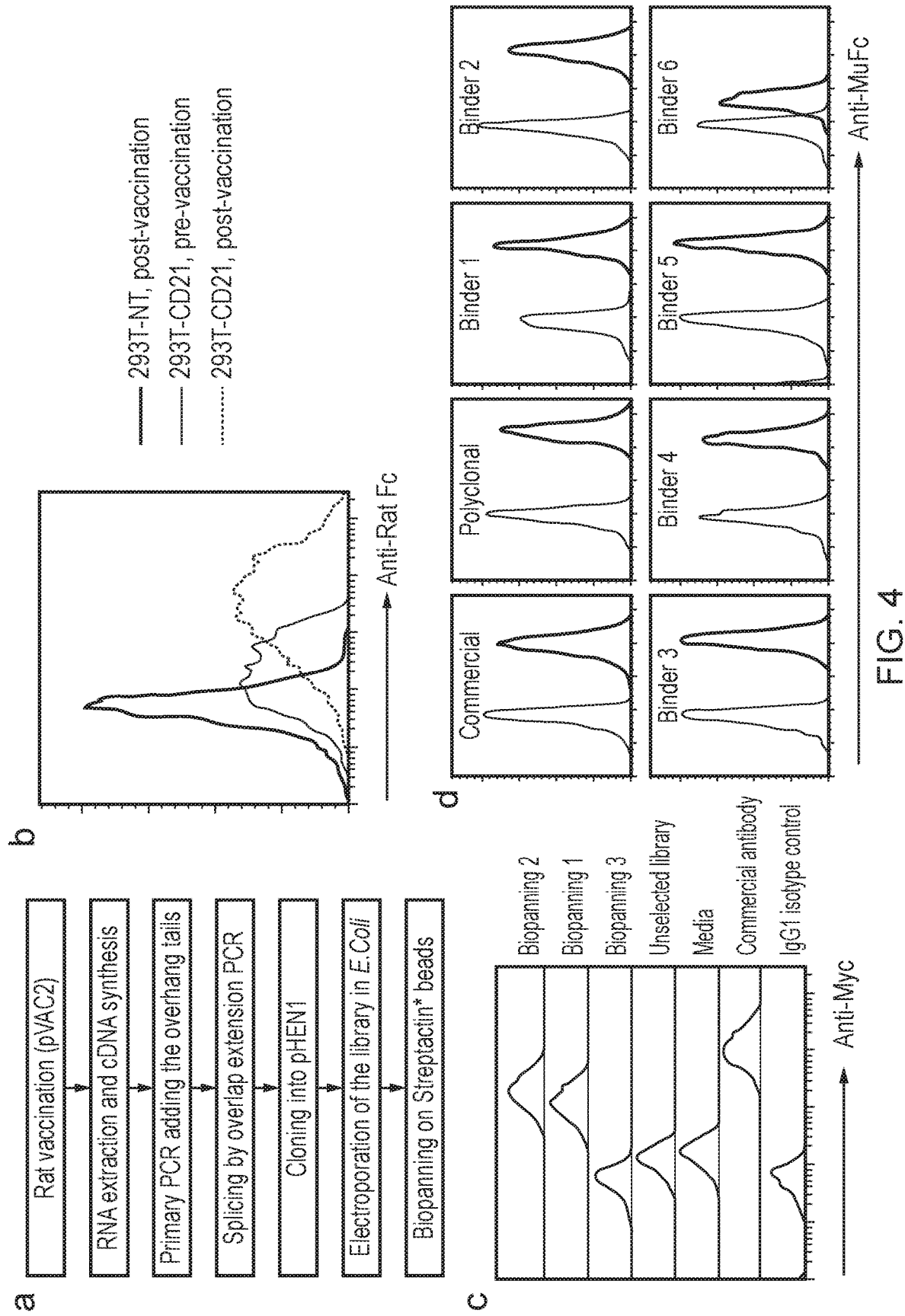
FIG. 4—Identification of anti-CD21 binders by genetic vaccination and phage display. (a) Schematic of protocol (b) Pre- and post-vaccination serum from 1 representative rat was incubated with untransfected 293T cells or 293T cells transfected with CD21, then stained with anti-rat Fc. (c) Myc-tagged phage from unselected library and after each round of CD21 biopanning was incubated with CD21+ Raji cells, then stained with anti-Myc. Enrichment of CD21 phage was seen. (d) Single phage clones from 3rd round of biopanning were cloned as ScFv-MuFc fusions, then incubated with non-transduced H9 cells (red, left-hand peak in each panel) or H9 cells transduced to express CD21 (blue, right-hand peak in each panel). (e) Binding kinetics of selected ScFv-Fc fusions to CD21 were evaluated by surface plasmon resonance. Variable heavy and light chain usage detailed.

Binders against human CD21 were isolated. Briefly, 3 rats were genetically vaccinated with human CD21. After confirmation of seroconversion against CD21 (FIG. 4B), lymphoid tissues were harvested, and B-cell RNA extracted. Immunoglobulin heavy and light chains were cloned into an immune phage-display library by PCR. This library was panned against beads coated with immobilised CD21 (FIG. 4C). 6 specific, high-affinity binders against CD21 were identified (FIG. 4D, Table 2 and Table 3).

Example 4—Illustrative CD21 CAR Functionality

Figure 5:
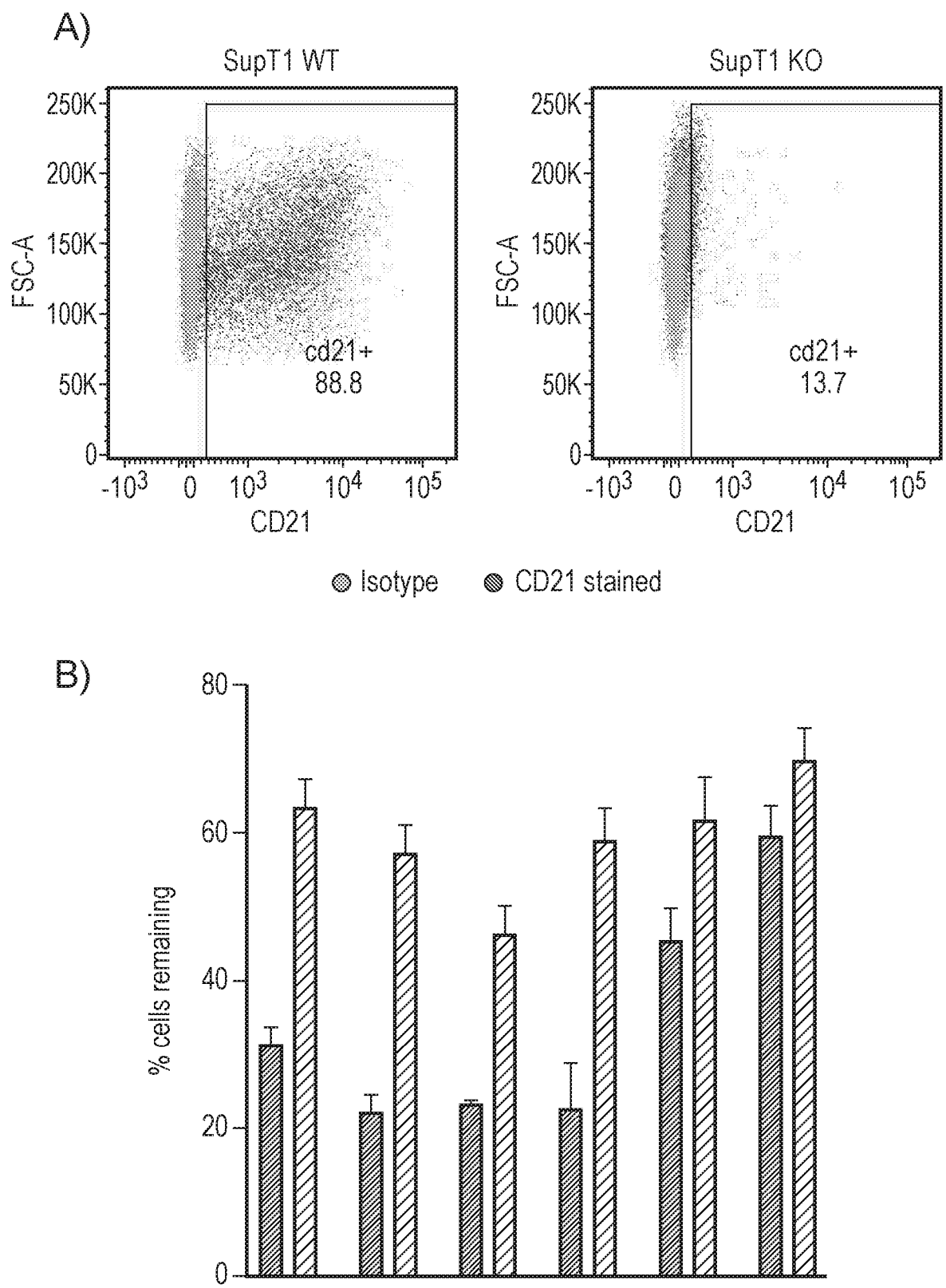
FIG. 5—Anti-CD21 CAR targeting the SupT1 T-cell leukaemia cell line. (a) A histogram of flow-cytometric analysis for SupT1 (a T-cell leukaemia cell line which expresses CD21) and SupT1 KO (a control cell line which was genomically edited at the CD21 locus to generate SupT1 derivative which was CD21 negative). (b) Normal donor human T-cells were transduced with anti-CD21 CAR derived from scFv C43 with a CD8 stalk spacer or an IgG1 hinge spacer, or with anti-CD21 CAR derived from scFv C48 with either a CD8 stalk spacer or an IgG1 hinge spacer. Control non-transduced T-cells and T-cells transduced with a CD19 CAR were also tested. These effectors were co-cultures with SupT1 targets or SupT1 cells which don't express CD21 target cells. Proportion of remaining targets is shown.

SupT1 is a T-cell leukaemia cell line which expresses CD21. To generate a control cell line which doesn't express CD21, SupT1 cells were genomically edited at the CD21 locus using CRISPR/Cas9 and a CD21 guide RNA which recognized the CD21 genomic. Wild-type and edited supT1 cells were stained with either an isotype antibody or an anti-CD21 antibody and analysed by flow-cytometry (see FIG. 5A).

Normal donor human T-cells were transduced (using retroviral constructs) with anti-CD21 CAR derived from scFv C43 with a CD8 stalk spacer or an IgG1 hinge spacer, or with anti-CD21 CAR derived from scFv C48 with either a CD8 stalk spacer or an IgG1 hinge spacer. Control non-transduced T-cells and T-cells transduced with a CD19 CAR were also tested.

Normal donor T-cells were isolated by ficoll, stimulated with soluble anti-CD3/anti-CD28 antibodies and retrovirally transduced with the above constructs. After transduction was confirmed by flow-cytometry, these effectors were co-cultures with SupT1 targets or SupT1 cells which don't express CD21 target cells. The co-culture was analyzed by flow cytometry calibrated by counting beads and remaining SupT1 cells were quantified (see FIG. 5B).

Example 5—CD21 Expression in T-ALL is Regulated in a NOTCH-Dependent Manner

Figure 6:
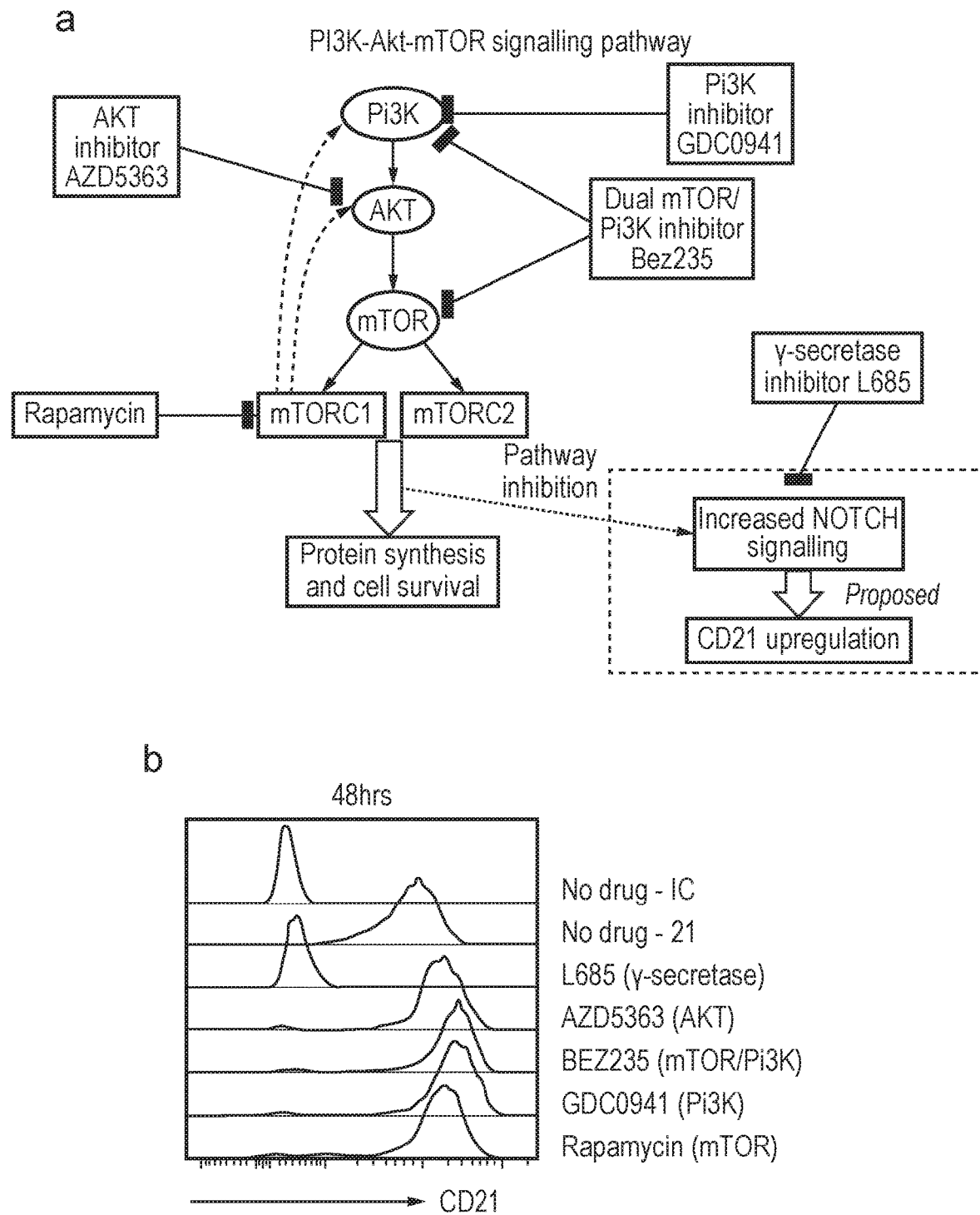
FIG. 6—Inhibition of PI3K-mTOR pathway in T-ALL cell lines leads to upregulation of CD21 expression. (a) Schematic of Pi3K/Akt/mTOR pathway. Solid blue lines with arrowheads—positive regulation, dotted blue lines (long dots)=negative regulation, solid red lines with block ends=drug inhibition. Dotted box=proposed mechanism for CD21 upregulation by drugs acting on PI3K/AKT/mTOR pathway. (b) CD21 expression in RPMI-8402 cell line after 48 hr co-culture with indicated drugs, targets in brackets IC=isotype control. (c) Fold change in CD21 protein surface copy number v no-drug condition on RPMI-8402 48 hrs after incubation with drugs acting on PI3K/AKT/mTOR pathway and for 48 hrs after drug has been removed.
Figure 6:
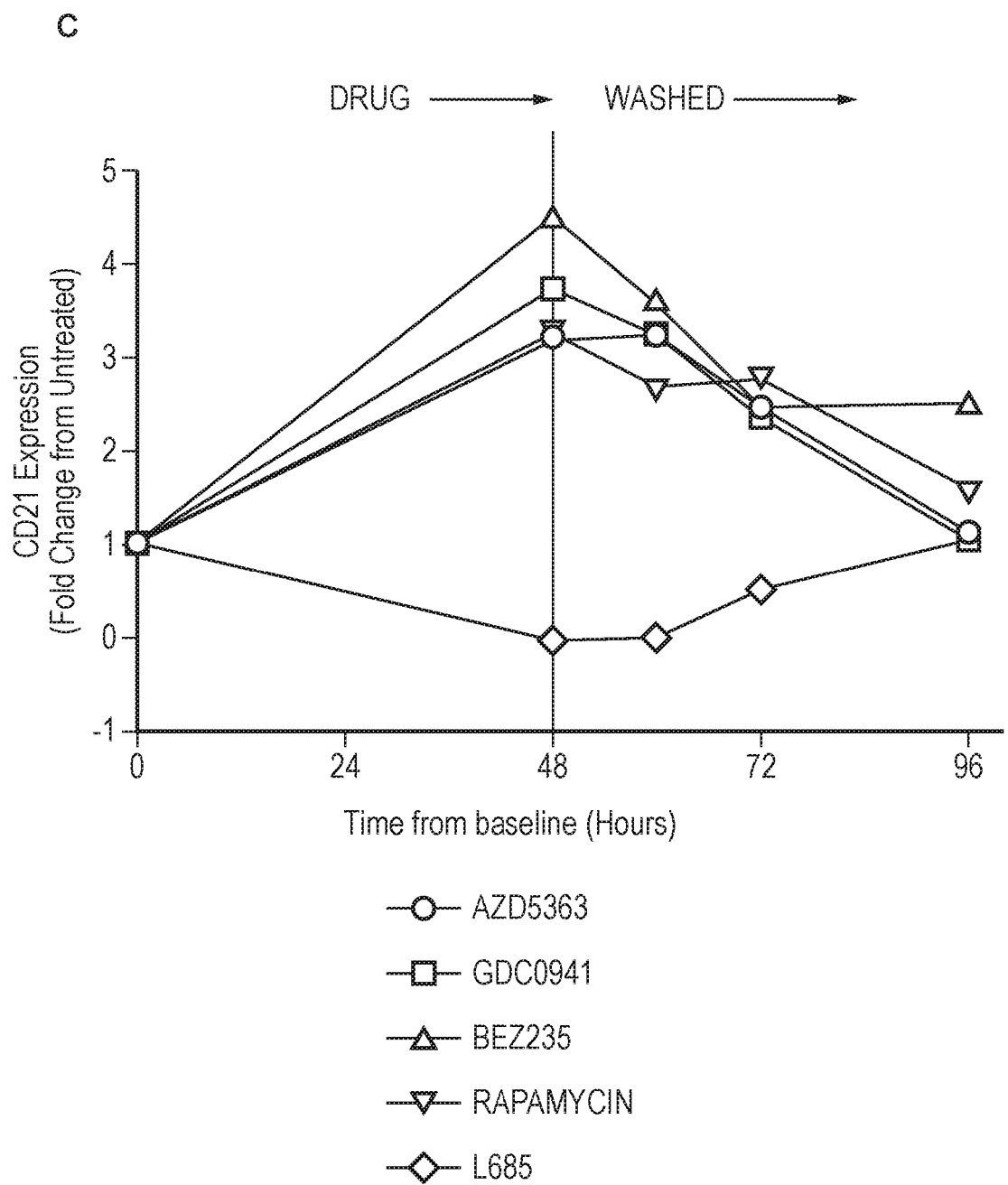

NOTCH mutated and unmutated cell lines incubated with multiple agents which block components of the PI3K/AKT/mTOR pathway confirms significant CD21 upregulation in NOTCH mutated T-ALL cell lines only, and loss of CD21 protein expression upon incubation with a gamma-secretase inhibitor, which inhibits NOTCH. This effect was seen to persist up to at least 24 hrs after the drug has been removed (see FIG. 6).

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A chimeric antigen receptor (CAR) comprising a CD21-binding domain, a transmembrane domain and an intracellular domain; wherein the CD21-binding domain comprises a variable heavy chain and a variable light chain comprising:
   (i) HCDR1, HDCR2 and HCDR3 of SEQ ID NOs: 2 to 4 and LCDR1, LDCR2 and LCDR3 of SEQ ID NOs: 15 to 17;
   (ii) HCDR1, HDCR2 and HCDR3 of SEQ ID NOs: 2, 5, 6 and LCDR1, LDCR2 and LCDR3 of SEQ ID NOs: 18 to 20;
   (iii) HCDR1, HDCR2 and HCDR3 of SEQ ID NOs: 7 to 9 and LCDR1, LDCR2 and LCDR3 of SEQ ID NOs: 21 to 23;
   (iv) HCDR1, HDCR2 and HCDR3 of SEQ ID NOs: 7 to 9 and LCDR1, LDCR2 and LCDR3 of SEQ ID NOs: 24 to 26;
   (v) HCDR1, HDCR2 and HCDR3 of SEQ ID NOs: 10 to 12 and LCDR1, LDCR2 and LCDR3 of SEQ ID NOs: 27 to 29; or
   (vi) HCDR1, HDCR2 and HCDR3 of SEQ ID NOs: 2, 13, 14, and LCDR1, LDCR2 and LCDR3 of SEQ ID NOs: 21, 57 and 23.

2. A CAR according to claim 1 wherein the CD21-binding domain is a scFv.

3. A CAR according to claim 1 wherein the six CDR sequences are grafted onto a human antibody framework sequence.

4. A CAR according to claim 1 wherein the CD21-binding domain comprises an amino acid sequence shown as any one of SEQ ID NO: 29-37 or a variant of any one of SEQ ID NO: 29-37 having at least 80% sequence identity thereto.

5. A CAR according to claim 1 wherein the intracellular domain comprises a T cell signalling domain.

6. A polynucleotide which encodes a CAR according to claim 1.

7. A vector which comprises a polynucleotide according to claim 6.

8. A cell expressing a CAR according to claim 1.

9. A pharmaceutical composition which comprises a CAR according to claim 1.

10. A method for treating a disease, which comprises the step of administering a cell expressing a CAR according to claim 8 to a subject in need thereof, wherein the disease is a CD21 positive T-cell acute lymphoblastic leukemia, a CD21 positive B-cell leukemia or a CD21 positive B-cell lymphoma.

11. The method according to claim 10, which comprises the following steps:
    (i) isolation of a cell containing sample;
    (ii) transduction or transfection of the cell with a polynucleotide according to claim 6 or a vector according to claim 7; and
    (iii) administering the cells from (ii) to a subject.

12. The method according to claim 11 wherein the cell is autologous or wherein the cell is allogenic.

13. The method according to claim 10 wherein the cell is administered in combination with a NOTCH activating agent.

14. The method according to claim 13 wherein the cell and the NOTCH activating agent are administered simultaneously, sequentially or separately.

15. A kit comprising (i) a CAR according to claim 1; and (ii) a NOTCH activating agent.

* * * * *

SEQUENCE LISTING

```
<160> NUMBER OF SEQ ID NOS: 64

<210> SEQ ID NO 1
<211> LENGTH: 1032
<212> TYPE: PRT
<213> ORGANISM: Homo sapiens

<400> SEQUENCE: 1

Met Gly Ala Ala Gly Leu Leu Gly Val Phe Leu Ala Leu Val Ala Pro
1               5                   10                  15

Gly Val Leu Gly Ile Ser Cys Gly Ser Pro Pro Pro Ile Leu Asn Gly
                20                  25                  30

Arg Ile Ser Tyr Tyr Ser Thr Pro Ile Ala Val Gly Thr Val Ile Arg
            35                  40                  45

Tyr Ser Cys Ser Gly Thr Phe Arg Leu Ile Gly Glu Lys Ser Leu Leu
        50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
            100                 105                 110

Ser Val Thr Phe Ala Cys Lys Thr Asn Phe Ser Met Asn Gly Asn Lys
        115                 120                 125

Ser Val Trp Cys Gln Ala Asn Asn Met Trp Gly Pro Thr Arg Leu Pro
    130                 135                 140
```

-continued

```
Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
            165                 170                 175

Leu Ser Val Thr Tyr Ser Cys Glu Ser Gly Tyr Leu Leu Val Gly Glu
            180                 185                 190

Lys Ile Ile Asn Cys Leu Ser Ser Gly Lys Trp Ser Ala Val Pro Pro
            195                 200                 205

Thr Cys Glu Glu Ala Arg Cys Lys Ser Leu Gly Arg Phe Pro Asn Gly
210                 215                 220

Lys Val Lys Glu Pro Pro Ile Leu Arg Val Gly Val Thr Ala Asn Phe
225                 230                 235                 240

Phe Cys Asp Glu Gly Tyr Arg Leu Gln Gly Pro Pro Ser Ser Arg Cys
            245                 250                 255

Val Ile Ala Gly Gln Gly Val Ala Trp Thr Lys Met Pro Val Cys Glu
            260                 265                 270

Glu Ile Phe Cys Pro Ser Pro Pro Ile Leu Asn Gly Arg His Ile
            275                 280                 285

Gly Asn Ser Leu Ala Asn Val Ser Tyr Gly Ser Ile Val Thr Tyr Thr
290                 295                 300

Cys Asp Pro Asp Pro Glu Glu Gly Val Asn Phe Ile Leu Ile Gly Glu
305                 310                 315                 320

Ser Thr Leu Arg Cys Thr Val Asp Ser Gln Lys Thr Gly Thr Trp Ser
            325                 330                 335

Gly Pro Ala Pro Arg Cys Glu Leu Ser Thr Ser Ala Val Gln Cys Pro
            340                 345                 350

His Pro Gln Ile Leu Arg Gly Arg Met Val Ser Gly Gln Lys Asp Arg
            355                 360                 365

Tyr Thr Tyr Asn Asp Thr Val Ile Phe Ala Cys Met Phe Gly Phe Thr
            370                 375                 380

Leu Lys Gly Ser Lys Gln Ile Arg Cys Asn Ala Gln Gly Thr Trp Glu
385                 390                 395                 400

Pro Ser Ala Pro Val Cys Glu Lys Glu Cys Gln Ala Pro Pro Asn Ile
            405                 410                 415

Leu Asn Gly Gln Lys Glu Asp Arg His Met Val Arg Phe Asp Pro Gly
            420                 425                 430

Thr Ser Ile Lys Tyr Ser Cys Asn Pro Gly Tyr Val Leu Val Gly Glu
            435                 440                 445

Glu Ser Ile Gln Cys Thr Ser Glu Gly Val Trp Thr Pro Pro Val Pro
450                 455                 460

Gln Cys Lys Val Ala Ala Cys Glu Ala Thr Gly Arg Gln Leu Leu Thr
465                 470                 475                 480

Lys Pro Gln His Gln Phe Val Arg Pro Asp Val Asn Ser Ser Cys Gly
            485                 490                 495

Glu Gly Tyr Lys Leu Ser Gly Ser Val Tyr Gln Glu Cys Gln Gly Thr
            500                 505                 510

Ile Pro Trp Phe Met Glu Ile Arg Leu Cys Lys Glu Ile Thr Cys Pro
            515                 520                 525

Pro Pro Pro Val Ile Tyr Asn Gly Ala His Thr Gly Ser Ser Leu Glu
530                 535                 540

Asp Phe Pro Tyr Gly Thr Thr Val Thr Tyr Thr Cys Asn Pro Gly Pro
545                 550                 555                 560

Glu Arg Gly Val Glu Phe Ser Leu Ile Gly Glu Ser Thr Ile Arg Cys
```

-continued

```
                565                 570                 575
Thr Ser Asn Asp Gln Glu Arg Gly Thr Trp Ser Gly Pro Ala Pro Leu
            580                 585                 590
Cys Lys Leu Ser Leu Leu Ala Val Gln Cys Ser His Val His Ile Ala
            595                 600                 605
Asn Gly Tyr Lys Ile Ser Lys Glu Ala Pro Tyr Phe Tyr Asn Asp
            610                 615                 620
Thr Val Thr Phe Lys Cys Tyr Ser Gly Phe Thr Leu Lys Gly Ser Ser
625                 630                 635                 640
Gln Ile Arg Cys Lys Ala Asp Asn Thr Trp Asp Pro Glu Ile Pro Val
                645                 650                 655
Cys Glu Lys Glu Thr Cys Gln His Val Arg Gln Ser Leu Gln Glu Leu
                660                 665                 670
Pro Ala Gly Ser Arg Val Glu Leu Val Asn Thr Ser Cys Gln Asp Gly
                675                 680                 685
Tyr Gln Leu Thr Gly His Ala Tyr Gln Met Cys Gln Asp Ala Glu Asn
            690                 695                 700
Gly Ile Trp Phe Lys Lys Ile Pro Leu Cys Lys Val Ile His Cys His
705                 710                 715                 720
Pro Pro Pro Val Ile Val Asn Gly Lys His Thr Gly Met Met Ala Glu
                725                 730                 735
Asn Phe Leu Tyr Asn Glu Val Ser Tyr Glu Cys Asp Gln Gly Phe Tyr
            740                 745                 750
Leu Leu Gly Glu Lys Lys Leu Gln Cys Arg Ser Asp Ser Lys Gly His
            755                 760                 765
Gly Ser Trp Ser Gly Pro Ser Pro Gln Cys Leu Arg Ser Pro Pro Val
770                 775                 780
Thr Arg Cys Pro Asn Pro Glu Val Lys His Gly Tyr Lys Leu Asn Lys
785                 790                 795                 800
Thr His Ser Ala Tyr Ser His Asn Asp Ile Val Tyr Val Asp Cys Asn
                805                 810                 815
Pro Gly Phe Ile Met Asn Gly Ser Arg Val Ile Arg Cys His Thr Asp
            820                 825                 830
Asn Thr Trp Val Pro Gly Val Pro Thr Cys Ile Lys Lys Ala Phe Ile
            835                 840                 845
Gly Cys Pro Pro Pro Lys Thr Pro Asn Gly Asn His Thr Gly Gly
850                 855                 860
Asn Ile Ala Arg Phe Ser Pro Gly Met Ser Ile Leu Tyr Ser Cys Asp
865                 870                 875                 880
Gln Gly Tyr Leu Leu Val Gly Glu Ala Leu Leu Leu Cys Thr His Glu
                885                 890                 895
Gly Thr Trp Ser Gln Pro Ala Pro His Cys Lys Glu Val Asn Cys Ser
                900                 905                 910
Ser Pro Ala Asp Met Asp Gly Ile Gln Lys Gly Leu Glu Pro Arg Lys
            915                 920                 925
Met Tyr Gln Tyr Gly Ala Val Val Thr Leu Glu Cys Glu Asp Gly Tyr
            930                 935                 940
Met Leu Glu Gly Ser Pro Gln Ser Gln Cys Gln Ser Asp His Gln Trp
945                 950                 955                 960
Asn Pro Pro Leu Ala Val Cys Arg Ser Arg Ser Leu Ala Pro Val Leu
                965                 970                 975
Cys Gly Ile Ala Ala Gly Leu Ile Leu Leu Thr Phe Leu Ile Val Ile
                980                 985                 990
```

```
Thr Leu Tyr Val Ile Ser Lys His  Arg Ala Arg Asn Tyr  Tyr Thr Asp
        995                 1000                 1005

Thr Ser  Gln Lys Glu Ala Phe  His Leu Glu Ala Arg  Glu Val Tyr
    1010                 1015                 1020

Ser Val  Asp Pro Tyr Asn Pro  Ala Ser
    1025                 1030

<210> SEQ ID NO 2
<211> LENGTH: 7
<212> TYPE: PRT
<213> ORGANISM: Artificial Sequence
<220> FEATURE:
<223> OTHER INFORMATION: Clone MP27963 Variable Heavy Chain (VH)
      complementarity determining region (CDR) CDR1

<400> SEQUENCE: 2

Gly Tyr Thr Phe Thr Ser Asn
1               5

<210> SEQ ID NO 3
<211> LENGTH: 6
<212> TYPE: PRT
<213> ORGANISM: Artificial Sequence
<220> FEATURE:
<223> OTHER INFORMATION: Clone MP27963 VH CDR2

<400> SEQUENCE: 3

Ser Pro Gly Asp Gly Asp
1               5

<210> SEQ ID NO 4
<211> LENGTH: 13
<212> TYPE: PRT
<213> ORGANISM: Artificial Sequence
<220> FEATURE:
<223> OTHER INFORMATION: Clone MP27963 VH CDR3

<400> SEQUENCE: 4

Gly Asp Ser Ser Gly Trp Gly Pro Asn Trp Phe Asp Ser
1               5                   10

<210> SEQ ID NO 5
<211> LENGTH: 6
<212> TYPE: PRT
<213> ORGANISM: Artificial Sequence
<220> FEATURE:
<223> OTHER INFORMATION: Clone MP27964 VH CDR2

<400> SEQUENCE: 5

Tyr Pro Gly Asp Gly Asp
1               5

<210> SEQ ID NO 6
<211> LENGTH: 8
<212> TYPE: PRT
<213> ORGANISM: Artificial Sequence
<220> FEATURE:
<223> OTHER INFORMATION: Clone MP27964 VH CDR3

<400> SEQUENCE: 6

Ser Gly Asp Gly Tyr Phe Asp Tyr
1               5

<210> SEQ ID NO 7
<211> LENGTH: 7
```

```
<212> TYPE: PRT
<213> ORGANISM: Artificial Sequence
<220> FEATURE:
<223> OTHER INFORMATION: Clone MP27965 VH CDR1

<400> SEQUENCE: 7

Gly Tyr Thr Phe Thr Thr Asn
1               5

<210> SEQ ID NO 8
<211> LENGTH: 6
<212> TYPE: PRT
<213> ORGANISM: Artificial Sequence
<220> FEATURE:
<223> OTHER INFORMATION: Clone MP27965 VH CDR2

<400> SEQUENCE: 8

Asn Pro Gly Asp Gly Asn
1               5

<210> SEQ ID NO 9
<211> LENGTH: 13
<212> TYPE: PRT
<213> ORGANISM: Artificial Sequence
<220> FEATURE:
<223> OTHER INFORMATION: Clone MP27965 VH CDR3

<400> SEQUENCE: 9

Gly Asp Tyr Ser Gly Trp Gly Pro Asn Trp Phe Asp Tyr
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Clone MP27967 VH CDR1

<400> SEQUENCE: 10

Gly Tyr Asn Ile Arg Asn Thr
1               5

<210> SEQ ID NO 11
<211> LENGTH: 7
<212> TYPE: PRT
<213> ORGANISM: Artificial Sequence
<220> FEATURE:
<223> OTHER INFORMATION: Clone MP27967 VH CDR2

<400> SEQUENCE: 11

Asp Pro Ala Asn Gly Asp Thr
1               5

<210> SEQ ID NO 12
<211> LENGTH: 12
<212> TYPE: PRT
<213> ORGANISM: Artificial Sequence
<220> FEATURE:
<223> OTHER INFORMATION: Clone MP27967 VH CDR3

<400> SEQUENCE: 12

Arg Met Val Gly Thr Gly Gly Tyr Ala Met Asp Ala
1               5                   10

<210> SEQ ID NO 13
<211> LENGTH: 6
<212> TYPE: PRT
```

```
<213> ORGANISM: Artificial Sequence
<220> FEATURE:
<223> OTHER INFORMATION: Clone MP28132 VH CDR2

<400> SEQUENCE: 13

Tyr Arg Gly Asp Gly Asp
1               5

<210> SEQ ID NO 14
<211> LENGTH: 13
<212> TYPE: PRT
<213> ORGANISM: Artificial Sequence
<220> FEATURE:
<223> OTHER INFORMATION: Clone MP28132 VH CDR3

<400> SEQUENCE: 14

Gly Asp Ser Ser Gly Trp Gly Pro Asn Trp Phe Asp Ser
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Clone MP27963 Variable Light Chain (VL) CDR1

<400> SEQUENCE: 15

Leu Ala Ser Gln Asp Ile Gly Asn Tyr Leu Ser
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Clone MP27963 VL CDR2

<400> SEQUENCE: 16

Asp Val Asn Asn Leu Glu Asp
1               5

<210> SEQ ID NO 17
<211> LENGTH: 9
<212> TYPE: PRT
<213> ORGANISM: Artificial Sequence
<220> FEATURE:
<223> OTHER INFORMATION: Clone MP27963 VL CDR3

<400> SEQUENCE: 17

Gln Gln Tyr Tyr Glu Tyr Pro Leu Thr
1               5

<210> SEQ ID NO 18
<211> LENGTH: 10
<212> TYPE: PRT
<213> ORGANISM: Artificial Sequence
<220> FEATURE:
<223> OTHER INFORMATION: Clone MP27964 VL CDR1

<400> SEQUENCE: 18

Arg Val Ser Ser Ser Val Ser Tyr Met His
1               5                   10

<210> SEQ ID NO 19
<211> LENGTH: 7
<212> TYPE: PRT
<213> ORGANISM: Artificial Sequence
```

```
<220> FEATURE:
<223> OTHER INFORMATION: Clone MP27964 VL CDR2

<400> SEQUENCE: 19

Glu Thr Ser Lys Leu Ala Ser
1               5

<210> SEQ ID NO 20
<211> LENGTH: 8
<212> TYPE: PRT
<213> ORGANISM: Artificial Sequence
<220> FEATURE:
<223> OTHER INFORMATION: Clone MP27964 VL CDR3

<400> SEQUENCE: 20

Gln Gln Trp Asn Phe Pro Leu Thr
1               5

<210> SEQ ID NO 21
<211> LENGTH: 11
<212> TYPE: PRT
<213> ORGANISM: Artificial Sequence
<220> FEATURE:
<223> OTHER INFORMATION: Clone MP27965 VL CDR1

<400> SEQUENCE: 21

Arg Ala Ser Glu Asp Ile Tyr Ser Asn Leu Ala
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Clone MP27965 VL CDR2

<400> SEQUENCE: 22

Asp Ala Asn Asn Leu Ala Asp
1               5

<210> SEQ ID NO 23
<211> LENGTH: 9
<212> TYPE: PRT
<213> ORGANISM: Artificial Sequence
<220> FEATURE:
<223> OTHER INFORMATION: Clone MP27965 VL CDR3

<400> SEQUENCE: 23

Gln Gln Tyr Asn Asn Tyr Pro Leu Thr
1               5

<210> SEQ ID NO 24
<211> LENGTH: 11
<212> TYPE: PRT
<213> ORGANISM: Artificial Sequence
<220> FEATURE:
<223> OTHER INFORMATION: Clone MP27966 VL CDR1

<400> SEQUENCE: 24

Leu Ala Ser Gln Asp Ile Gly Asp Tyr Leu Ser
1               5                   10

<210> SEQ ID NO 25
<211> LENGTH: 7
<212> TYPE: PRT
<213> ORGANISM: Artificial Sequence
<220> FEATURE:
```

```
<223> OTHER INFORMATION: Clone MP27966 VL CDR2

<400> SEQUENCE: 25

Gly Ala Thr Asn Leu Glu Asp
1               5

<210> SEQ ID NO 26
<211> LENGTH: 9
<212> TYPE: PRT
<213> ORGANISM: Artificial Sequence
<220> FEATURE:
<223> OTHER INFORMATION: Clone MP27966 VL CDR3

<400> SEQUENCE: 26

His Gln Tyr Tyr Gln Tyr Pro Leu Thr
1               5

<210> SEQ ID NO 27
<211> LENGTH: 15
<212> TYPE: PRT
<213> ORGANISM: Artificial Sequence
<220> FEATURE:
<223> OTHER INFORMATION: Clone MP27967 VL CDR1

<400> SEQUENCE: 27

Arg Ala Ser Gln Ser Val Ser Ile Ser Ser Val Asn Leu Met Asn
1               5                   10                  15

<210> SEQ ID NO 28
<211> LENGTH: 7
<212> TYPE: PRT
<213> ORGANISM: Artificial Sequence
<220> FEATURE:
<223> OTHER INFORMATION: Clone MP27967 VL CDR2

<400> SEQUENCE: 28

His Ala Ser Asn Leu Ala Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Clone MP27967 VL CDR3

<400> SEQUENCE: 29

Gln Gln Ser Arg Glu Ser Pro Trp Thr
1               5

<210> SEQ ID NO 30
<211> LENGTH: 238
<212> TYPE: PRT
<213> ORGANISM: Artificial Sequence
<220> FEATURE:
<223> OTHER INFORMATION: single-chain variable fragment (scFv) sequence

<400> SEQUENCE: 30

Glu Val His Leu Gln Gln Ser Gly Ala Glu Leu Val Lys Pro Gly Ser
1               5                   10                  15

Ser Val Lys Ile Ser Cys Lys Ala Ser Gly Tyr Thr Phe Thr Ser Asn
                20                  25                  30

Phe Met His Trp Ile Lys Gln Gln Pro Gly Asn Gly Leu Glu Trp Ile
            35                  40                  45

Gly Trp Ile Tyr Pro Gly Asp Gly Asp Thr Glu Tyr Asn Gln Lys Phe
```

Asn Gly Lys Ala Ser Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Leu Ser Gly Asp Gly Tyr Phe Asp Tyr Trp Gly Gln Gly Val Met
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Thr Thr Met Thr
130                 135                 140

Ala Ser Pro Gly Glu Lys Val Thr Ile Thr Cys Arg Val Ser Ser Ser
145                 150                 155                 160

Val Ser Tyr Met His Trp Tyr Gln Gln Lys Pro Asp Ala Ser Pro Lys
                165                 170                 175

Pro Trp Ile Tyr Glu Thr Ser Lys Leu Ala Ser Gly Val Pro Asp Arg
            180                 185                 190

Phe Ser Gly Ser Gly Ser Gly Thr Ser Tyr Ser Leu Thr Ile Asn Asn
        195                 200                 205

Met Glu Ala Glu Asp Ala Ala Thr Tyr Tyr Cys Gln Gln Trp Asn Phe
    210                 215                 220

Pro Leu Thr Phe Gly Ser Gly Thr Lys Leu Glu Ile Lys Arg
225                 230                 235

<210> SEQ ID NO 31
<211> LENGTH: 245
<212> TYPE: PRT
<213> ORGANISM: Artificial Sequence
<220> FEATURE:
<223> OTHER INFORMATION: scFv sequence

<400> SEQUENCE: 31

Gln Val Gln Leu Gln Gln Ser Gly Ala Glu Leu Val Lys Pro Gly Ser
1               5                   10                  15

Ser Val Lys Ile Ser Cys Lys Ala Ser Gly Tyr Thr Phe Thr Thr Asn
            20                  25                  30

Phe Met His Trp Ile Lys Gln Gln Pro Gly Asn Gly Leu Glu Trp Ile
        35                  40                  45

Gly Trp Ile Asn Pro Gly Asp Gly Asn Thr Glu Tyr Asn Gln Lys Phe
    50                  55                  60

Asn Val Lys Ala Thr Leu Thr Ala Asp Lys Ser Ser Thr Ala Tyr
65                  70                  75                  80

Met Glu Leu Gly Ser Leu Thr Ser Glu Asp Ser Ala Val Tyr Phe Cys
                85                  90                  95

Ala Arg Gly Asp Tyr Ser Gly Trp Gly Pro Asn Trp Phe Asp Tyr Trp
            100                 105                 110

Gly Gln Gly Thr Leu Val Thr Val Ser Ser Asp Gly Gly Gly Ser Gly
        115                 120                 125

Gly Gly Gly Ser Gly Gly Gly Ser Asp Ile Gln Met Thr Gln Ser
130                 135                 140

Pro Ala Ser Leu Ser Ala Ser Leu Gly Glu Thr Val Thr Ile Glu Cys
145                 150                 155                 160

Arg Ala Ser Glu Asp Ile Tyr Ser Asn Leu Ala Trp Tyr Gln Gln Lys
                165                 170                 175

Pro Gly Asn Ser Pro Gln Leu Leu Ile His Asp Ala Asn Asn Leu Ala

-continued

```
                180                 185                 190
Asp Gly Val Pro Ser Arg Phe Ser Gly Ser Gly Ser Gly Thr Gln Tyr
            195                 200                 205

Ser Leu Lys Ile Asn Ser Leu Gln Ser Glu Asp Val Ala Ser Tyr Phe
        210                 215                 220

Cys Gln Gln Tyr Asn Asn Tyr Pro Leu Thr Phe Gly Ser Gly Thr Lys
225                 230                 235                 240

Leu Glu Ile Lys Arg
            245

<210> SEQ ID NO 32
<211> LENGTH: 245
<212> TYPE: PRT
<213> ORGANISM: Artificial Sequence
<220> FEATURE:
<223> OTHER INFORMATION: scFv sequence

<400> SEQUENCE: 32

Gln Val Gln Leu Gln Gln Ser Gly Ala Glu Leu Val Lys Pro Gly Ser
1               5                   10                  15

Ser Val Lys Ile Ser Cys Lys Ala Ser Gly Tyr Thr Phe Thr Thr Asn
            20                  25                  30

Phe Met His Trp Ile Lys Gln Gln Pro Gly Asn Gly Leu Glu Trp Ile
        35                  40                  45

Gly Trp Ile Asn Pro Gly Asp Gly Asn Thr Glu Tyr Asn Gln Lys Phe
    50                  55                  60

Asn Val Lys Ala Thr Leu Thr Ala Asp Lys Ser Ser Ser Thr Ala Tyr
65                  70                  75                  80

Met Glu Leu Gly Ser Leu Thr Ser Glu Asp Ser Ala Val Tyr Phe Cys
                85                  90                  95

Ala Arg Gly Asp Tyr Ser Gly Trp Gly Pro Asn Trp Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Asp Ile Gln Leu Thr Gln Ser
    130                 135                 140

Pro Ser Ser Met Ser Ala Ser Leu Gly Asp Thr Val Thr Ile Thr Cys
145                 150                 155                 160

Leu Ala Ser Gln Asp Ile Gly Asp Tyr Leu Ser Trp Tyr Gln Gln Lys
                165                 170                 175

Pro Gly Lys Ser Pro Lys Val Met Val Tyr Gly Ala Thr Asn Leu Glu
            180                 185                 190

Asp Gly Val Pro Ser Arg Phe Ser Gly Arg Ser Gly Ser Asp Tyr
        195                 200                 205

Ser Leu Thr Ile Asn Ser Leu Gly Tyr Asp Asp Glu Gly Ile Tyr His
    210                 215                 220

Cys His Gln Tyr Tyr Gln Tyr Pro Leu Thr Phe Gly Ser Gly Thr Lys
225                 230                 235                 240

Leu Glu Ile Lys Arg
            245

<210> SEQ ID NO 33
<211> LENGTH: 247
<212> TYPE: PRT
<213> ORGANISM: Artificial Sequence
<220> FEATURE:
<223> OTHER INFORMATION: scFv sequence
```

<400> SEQUENCE: 33

```
Glu Val Gln Leu Gln Gln Ser Gly Ala Glu Leu Gly Lys Pro Gly Thr
1               5                  10                  15

Ser Val Lys Leu Ser Cys Lys Val Ser Gly Tyr Asn Ile Arg Asn Thr
            20                  25                  30

Tyr Ile His Trp Val Asn Gln Arg Pro Gly Lys Gly Leu Glu Trp Ile
        35                  40                  45

Gly Arg Ile Asp Pro Ala Asn Gly Asp Thr Ile Tyr Ala Glu Lys Phe
    50                  55                  60

Lys Ser Lys Ala Thr Leu Thr Ala Asp Thr Ser Ser Asn Thr Ala Tyr
65                  70                  75                  80

Met Gln Leu Ser Gln Leu Lys Ser Asp Asp Thr Ala Ile Tyr Phe Cys
                85                  90                  95

Ala Met Arg Met Val Gly Thr Gly Tyr Ala Met Asp Ala Trp Gly
            100                 105                 110

Gln Gly Ala Ser Val Thr Val Ser Ser Gly Gly Gly Ser Gly Gly
            115                 120                 125

Gly Gly Ser Gly Gly Gly Ser Asp Ile Val Leu Thr Gln Ser Pro
        130                 135                 140

Ala Leu Ala Val Ser Pro Gly Gln Arg Ala Thr Ile Ser Cys Arg Ala
145                 150                 155                 160

Ser Gln Ser Val Ser Ile Ser Ser Val Asn Leu Met Asn Trp Tyr Gln
                165                 170                 175

Gln Lys Pro Gly Gln Gln Pro Lys Leu Leu Ile Tyr His Ala Ser Asn
            180                 185                 190

Leu Ala Ser Gly Ile Pro Thr Arg Phe Ser Gly Ser Gly Ser Gly Thr
        195                 200                 205

Asp Phe Thr Leu Thr Ile Asp Pro Val Gln Ala Asp Asp Ile Ala Thr
    210                 215                 220

Tyr Tyr Cys Gln Gln Ser Arg Glu Ser Pro Trp Thr Phe Gly Gly Gly
225                 230                 235                 240

Thr Lys Leu Glu Leu Lys Arg
                245
```

<210> SEQ ID NO 34
<211> LENGTH: 245
<212> TYPE: PRT
<213> ORGANISM: Artificial Sequence
<220> FEATURE:
<223> OTHER INFORMATION: scFv sequence

<400> SEQUENCE: 34

```
Gln Val Gln Leu Gln Gln Ser Gly Ala Glu Leu Val Glu Pro Gly Ser
1               5                  10                  15

Ser Val Lys Ile Ser Cys Lys Ala Ser Gly Tyr Thr Phe Thr Ser Asn
            20                  25                  30

Phe Met His Trp Ile Arg Gln Gln Pro Gly Asn Gly Leu Glu Trp Ile
        35                  40                  45

Gly Trp Val Tyr Arg Gly Asp Gly Asp Thr Glu Tyr Asn Gln Arg Phe
    50                  55                  60

Asn Gly Lys Ala Thr Leu Thr Ala Asp Glu Ser Ser Thr Ala Tyr
65                  70                  75                  80

Ile Gln Leu Ser Gly Leu Thr Ser Glu Asp Ser Ala Val Tyr Phe Cys
                85                  90                  95
```

```
Ala Arg Gly Asp Ser Ser Gly Trp Gly Pro Asn Trp Phe Asp Ser Trp
            100                 105                 110

Gly Gln Gly Thr Leu Val Thr Val Ser Gly Gly Gly Ser Gly
        115                 120                 125

Gly Gly Gly Ser Gly Gly Gly Ser Asp Val Gln Met Thr Gln Ser
        130                 135                 140

Pro Ala Ser Leu Ser Ala Ser Leu Gly Glu Thr Val Thr Ile Glu Cys
145                 150                 155                 160

Arg Ala Ser Glu Asp Ile Tyr Ser Asn Leu Ala Trp Tyr Gln Gln Lys
                165                 170                 175

Pro Gly Asn Ser Pro Gln Leu Leu Ile Tyr Asp Ala Asn Ser Leu Ala
                180                 185                 190

Asp Gly Val Pro Ser Arg Phe Ser Gly Ser Gly Ser Gly Thr Gln Tyr
            195                 200                 205

Ser Leu Lys Ile Asn Ser Leu Gln Ser Glu Asp Val Ala Ser Tyr Phe
            210                 215                 220

Cys Gln Gln Tyr Asn Asn Tyr Pro Leu Thr Phe Gly Ser Glu Thr Arg
225                 230                 235                 240

Leu Glu Ile Lys Arg
            245
```

<210> SEQ ID NO 35
<211> LENGTH: 235
<212> TYPE: PRT
<213> ORGANISM: Artificial Sequence
<220> FEATURE:
<223> OTHER INFORMATION: scFv sequence

<400> SEQUENCE: 35

```
Gln Val Gln Leu Gln Gln Ser Gly Ala Gln Leu Val Lys Pro Gly Ser
1               5                   10                  15

Ser Val Lys Leu Ser Cys Lys Thr Ser Gly Phe Thr Phe Ser Ser Ser
            20                  25                  30

Tyr Ile Ser Trp Leu Lys Gln Ala Pro Gly Gln Ser Phe Glu Trp Ile
        35                  40                  45

Gly Asn Ile Phe Ala Gly Asp Gly Gly Pro Asn Tyr Ser Gln Lys Phe
    50                  55                  60

Lys Gly Lys Ala Thr Leu Thr Val Asp Thr Ser Ser Asn Thr Ala Tyr
65                  70                  75                  80

Met Asp Leu Ser Ser Leu Thr Ser Glu Asp Ser Ala Leu Tyr Phe Cys
                85                  90                  95

Ala Arg Pro Trp Ala Asn Trp Gly Gln Gly Thr Leu Val Thr Val Ser
            100                 105                 110

Ser Gly Gly Gly Gly Ser Gly Gly Gly Ser Gly Gly Gly Gly Ser
        115                 120                 125

Glu Ile Val Leu Thr Gln Ser Pro Thr Thr Ala Ala Ser Pro Gly
        130                 135                 140

Glu Lys Val Thr Ile Thr Cys Leu Ala Ser Ser Ser Ala Ser Asn Met
145                 150                 155                 160

Phe Trp Tyr Gln Gln Lys Ser Gly Asp Ser Pro Lys Leu Leu Ile Tyr
                165                 170                 175

Ser Thr Ser Ser Leu Ala Ser Gly Val Pro Asp Arg Phe Ser Gly Ser
            180                 185                 190

Gly Ser Gly Thr Ser Tyr Ser Leu Thr Ile Ser Ser Met Glu Ala Glu
            195                 200                 205
```

```
Asp Ala Ala Thr Tyr Tyr Cys Leu Gln Arg Ser Ser Tyr Pro Trp Thr
210                 215                 220

Phe Gly Gly Gly Thr Lys Leu Glu Leu Lys Arg
225                 230                 235
```

<210> SEQ ID NO 36
<211> LENGTH: 242
<212> TYPE: PRT
<213> ORGANISM: Artificial Sequence
<220> FEATURE:
<223> OTHER INFORMATION: scFv sequence

<400> SEQUENCE: 36

```
Glu Val Gln Leu Val Glu Thr Gly Gly Gly Leu Val Gln Pro Gly Lys
1               5                   10                  15

Ser Leu Lys Leu Thr Cys Ala Thr Ser Gly Phe Thr Phe Ser Thr Ala
                20                  25                  30

Trp Met His Trp Val Arg Gln Ser Pro Asp Lys Arg Leu Glu Trp Ile
            35                  40                  45

Ala Arg Ile Lys Asp Lys Ser Lys Asn Tyr Ala Thr Asp Tyr Val Glu
50                  55                  60

Ala Val Lys Gly Arg Phe Ser Ile Ser Arg Asp Asp Ser Lys Ser Ser
65                  70                  75                  80

Val Tyr Leu Gln Met Asn Ser Leu Lys Glu Glu Asp Thr Ala Thr Tyr
                85                  90                  95

Tyr Cys Thr Thr Gly Thr Tyr Arg Tyr Tyr Phe Asp Tyr Trp Gly Gln
            100                 105                 110

Gly Val Met Val Thr Val Ser Ser Gly Gly Gly Gly Ser Gly Gly Gly
        115                 120                 125

Gly Ser Gly Gly Gly Gly Ser Glu Ile Val Leu Thr Gln Ser Pro Thr
130                 135                 140

Thr Thr Ala Ala Ser Pro Gly Glu Lys Val Thr Ile Thr Cys Leu Ala
145                 150                 155                 160

Asn Ser Ser Val Ser Asn Met Tyr Trp Tyr Gln Gln Lys Ser Gly Ala
                165                 170                 175

Ser Pro Lys Leu Leu Ile Tyr Ser Thr Ser Arg Leu Ala Ser Gly Val
            180                 185                 190

Pro Asp Arg Phe Ser Gly Ser Gly Ser Gly Thr Ser Ser Ser Leu Thr
        195                 200                 205

Ile Asn Thr Met Glu Ala Glu Asp Ala Ala Thr Tyr Tyr Cys Gln Gln
210                 215                 220

Trp Ser Ser Asp Pro Pro Thr Phe Gly Ser Gly Thr Lys Leu Glu Leu
225                 230                 235                 240

Lys Arg
```

<210> SEQ ID NO 37
<211> LENGTH: 245
<212> TYPE: PRT
<213> ORGANISM: Artificial Sequence
<220> FEATURE:
<223> OTHER INFORMATION: scFv sequence

<400> SEQUENCE: 37

```
Gln Val Gln Leu Gln Gln Ser Gly Ala Glu Leu Ala Lys Pro Gly Ser
1               5                   10                  15

Ser Val Lys Ile Ser Cys Lys Ala Ser Gly Tyr Thr Phe Thr Asn Tyr
                20                  25                  30
```

His Ile Thr Trp Ile Lys Gln Thr Gly Gln Gly Leu Glu Tyr Val
            35                  40                  45

Gly Tyr Ile Asn Thr Gly Ser Gly Thr Thr Tyr Asn Glu Lys Phe
 50                  55                  60

Lys Gly Lys Ala Thr Leu Thr Val Asp Lys Ser Ser Thr Ala Phe
 65                  70                  75                  80

Met Gln Leu Ser Ser Leu Thr Pro Asp Asp Ser Ala Val Tyr Tyr Cys
                 85                  90                  95

Ala Arg Leu Val Leu His Trp Phe Ala Tyr Trp Gly Gln Gly Thr Leu
            100                 105                 110

Val Thr Val Ser Ser Gly Gly Gly Ser Gly Gly Gly Gly Ser Gly
            115                 120                 125

Gly Gly Ser Asp Ile Val Met Thr Gln Gly Ala Leu Pro Asn Pro
    130                 135                 140

Val Pro Ser Gly Glu Val Ala Ser Ile Thr Cys Gln Ser Ser Lys Ser
145                 150                 155                 160

Leu Leu His Ser Asn Gly Lys Thr Tyr Leu Asn Trp Tyr Leu Gln Arg
                165                 170                 175

Pro Gly Gln Ser Pro Gln Leu Leu Ile Tyr Trp Met Ser Thr Arg Ala
            180                 185                 190

Ser Gly Val Ser Asp Arg Phe Ser Gly Ser Gly Ser Gly Thr Asp Phe
            195                 200                 205

Thr Leu Lys Ile Ser Ser Val Glu Ala Glu Asp Val Gly Val Tyr Tyr
            210                 215                 220

Cys Gln Gln Phe Leu Glu Tyr Pro Arg Thr Phe Gly Gly Gly Thr Lys
225                 230                 235                 240

Leu Glu Leu Lys Arg
                245

<210> SEQ ID NO 38
<211> LENGTH: 122
<212> TYPE: PRT
<213> ORGANISM: Artificial Sequence
<220> FEATURE:
<223> OTHER INFORMATION: CD21-binding domain

<400> SEQUENCE: 38

Gln Val Gln Leu Gln Gln Ser Gly Ala Glu Leu Val Arg Pro Gly Ser
 1               5                  10                  15

Ser Val Lys Ile Ser Cys Lys Ala Ser Gly Tyr Thr Phe Thr Ser Asn
                20                  25                  30

Phe Met His Trp Ile Lys Gln Gln Pro Gly Asn Gly Leu Glu Trp Ile
            35                  40                  45

Gly Trp Ile Ser Pro Gly Asp Gly Asp Thr Glu Tyr Asn Gln Lys Phe
 50                  55                  60

Asn Gly Lys Ala Thr Leu Thr Ala Asp Glu Ser Ser Ser Thr Ala Tyr
 65                  70                  75                  80

Ile Gln Leu Ser Gly Leu Thr Ser Glu Asp Ser Ala Val Tyr Phe Cys
                85                  90                  95

Ala Arg Gly Asp Ser Ser Gly Trp Gly Pro Asn Trp Phe Asp Ser Trp
            100                 105                 110

Gly Gln Gly Thr Leu Val Thr Val Ser Ser
            115                 120

<210> SEQ ID NO 39
<211> LENGTH: 108

-continued

```
<212> TYPE: PRT
<213> ORGANISM: Artificial Sequence
<220> FEATURE:
<223> OTHER INFORMATION: CD21-binding domain

<400> SEQUENCE: 39

Asp Ile Gln Met Thr Gln Ser Pro Ser Ser Met Ser Ala Ser Leu Gly
1               5                   10                  15

Asp Thr Val Thr Ile Thr Cys Leu Ala Ser Gln Asp Ile Gly Asn Tyr
            20                  25                  30

Leu Ser Trp Tyr Gln Gln Lys Pro Gly Lys Ser Pro Lys Leu Met Ile
        35                  40                  45

Tyr Asp Val Asn Asn Leu Glu Asp Gly Val Pro Ser Arg Phe Ser Gly
50                  55                  60

Ser Arg Ser Gly Ser Asn His Ser Leu Thr Ile Asn Ser Leu Gly Tyr
65                  70                  75                  80

Asp Asp Glu Gly Ile Tyr His Cys Gln Gln Tyr Tyr Glu Tyr Pro Leu
                85                  90                  95

Thr Phe Gly Ser Gly Thr Lys Leu Glu Ile Lys Arg
            100                 105

<210> SEQ ID NO 40
<211> LENGTH: 117
<212> TYPE: PRT
<213> ORGANISM: Artificial Sequence
<220> FEATURE:
<223> OTHER INFORMATION: CD21-binding domain

<400> SEQUENCE: 40

Glu Val His Leu Gln Gln Ser Gly Ala Glu Leu Val Lys Pro Gly Ser
1               5                   10                  15

Ser Val Lys Ile Ser Cys Lys Ala Ser Gly Tyr Thr Phe Thr Ser Asn
            20                  25                  30

Phe Met His Trp Ile Lys Gln Gln Pro Gly Asn Gly Leu Glu Trp Ile
        35                  40                  45

Gly Trp Ile Tyr Pro Gly Asp Gly Asp Thr Glu Tyr Asn Gln Lys Phe
50                  55                  60

Asn Gly Lys Ala Ser Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Leu Ser Gly Asp Gly Tyr Phe Asp Tyr Trp Gly Gln Gly Val Met
            100                 105                 110

Val Thr Val Ser Ser
        115

<210> SEQ ID NO 41
<211> LENGTH: 106
<212> TYPE: PRT
<213> ORGANISM: Artificial Sequence
<220> FEATURE:
<223> OTHER INFORMATION: CD21-binding domain

<400> SEQUENCE: 41

Glu Ile Val Leu Thr Gln Ser Pro Thr Thr Met Thr Ala Ser Pro Gly
1               5                   10                  15

Glu Lys Val Thr Ile Thr Cys Arg Val Ser Ser Ser Val Ser Tyr Met
            20                  25                  30

His Trp Tyr Gln Gln Lys Pro Asp Ala Ser Pro Lys Pro Trp Ile Tyr
```

```
                35                  40                  45
Glu Thr Ser Lys Leu Ala Ser Gly Val Pro Asp Arg Phe Ser Gly Ser
         50                  55                  60

Gly Ser Gly Thr Ser Tyr Ser Leu Thr Ile Asn Asn Met Glu Ala Glu
65                  70                  75                  80

Asp Ala Ala Thr Tyr Tyr Cys Gln Gln Trp Asn Phe Pro Leu Thr Phe
                85                  90                  95

Gly Ser Gly Thr Lys Leu Glu Ile Lys Arg
        100                 105

<210> SEQ ID NO 42
<211> LENGTH: 121
<212> TYPE: PRT
<213> ORGANISM: Artificial Sequence
<220> FEATURE:
<223> OTHER INFORMATION: CD21-binding domain

<400> SEQUENCE: 42

Val Gln Leu Gln Gln Ser Gly Ala Glu Leu Val Lys Pro Gly Ser Ser
1               5                   10                  15

Val Lys Ile Ser Cys Lys Ala Ser Gly Tyr Thr Phe Thr Thr Asn Phe
                20                  25                  30

Met His Trp Ile Lys Gln Gln Pro Gly Asn Gly Leu Glu Trp Ile Gly
            35                  40                  45

Trp Ile Asn Pro Gly Asp Gly Asn Thr Glu Tyr Asn Gln Lys Phe Asn
        50                  55                  60

Val Lys Ala Thr Leu Thr Ala Asp Lys Ser Ser Ser Thr Ala Tyr Met
65                  70                  75                  80

Glu Leu Gly Ser Leu Thr Ser Glu Asp Ser Ala Val Tyr Phe Cys Ala
                85                  90                  95

Arg Gly Asp Tyr Ser Gly Trp Gly Pro Asn Trp Phe Asp Tyr Trp Gly
                100                 105                 110

Gln Gly Thr Leu Val Thr Val Ser Ser
            115                 120

<210> SEQ ID NO 43
<211> LENGTH: 108
<212> TYPE: PRT
<213> ORGANISM: Artificial Sequence
<220> FEATURE:
<223> OTHER INFORMATION: CD21-binding domain

<400> SEQUENCE: 43

Asp Ile Gln Met Thr Gln Ser Pro Ala Ser Leu Ser Ala Ser Leu Gly
1               5                   10                  15

Glu Thr Val Thr Ile Glu Cys Arg Ala Ser Glu Asp Ile Tyr Ser Asn
                20                  25                  30

Leu Ala Trp Tyr Gln Gln Lys Pro Gly Asn Ser Pro Gln Leu Leu Ile
            35                  40                  45

His Asp Ala Asn Asn Leu Ala Asp Gly Val Pro Ser Arg Phe Ser Gly
        50                  55                  60

Ser Gly Ser Gly Thr Gln Tyr Ser Leu Lys Ile Asn Ser Leu Gln Ser
65                  70                  75                  80

Glu Asp Val Ala Ser Tyr Phe Cys Gln Gln Tyr Asn Asn Tyr Pro Leu
                85                  90                  95

Thr Phe Gly Ser Gly Thr Lys Leu Glu Ile Lys Arg
            100                 105
```

<210> SEQ ID NO 44
<211> LENGTH: 122
<212> TYPE: PRT
<213> ORGANISM: Artificial Sequence
<220> FEATURE:
<223> OTHER INFORMATION: CD21-binding domain

<400> SEQUENCE: 44

```
Gln Val Gln Leu Gln Gln Ser Gly Ala Glu Leu Val Lys Pro Gly Ser
1               5                   10                  15

Ser Val Lys Ile Ser Cys Lys Ala Ser Gly Tyr Thr Phe Thr Thr Asn
                20                  25                  30

Phe Met His Trp Ile Lys Gln Pro Gly Asn Gly Leu Glu Trp Ile
            35                  40                  45

Gly Trp Ile Asn Pro Gly Asp Gly Asn Thr Glu Tyr Asn Gln Lys Phe
    50                  55                  60

Asn Val Lys Ala Thr Leu Thr Ala Asp Lys Ser Ser Thr Ala Tyr
65                  70                  75                  80

Met Glu Leu Gly Ser Leu Thr Ser Glu Asp Ser Ala Val Tyr Phe Cys
                85                  90                  95

Ala Arg Gly Asp Tyr Ser Gly Trp Gly Pro Asn Trp Phe Asp Tyr Trp
            100                 105                 110

Gly Gln Gly Thr Leu Val Thr Val Ser Ser
        115                 120
```

<210> SEQ ID NO 45
<211> LENGTH: 108
<212> TYPE: PRT
<213> ORGANISM: Artificial Sequence
<220> FEATURE:
<223> OTHER INFORMATION: CD21-binding domain

<400> SEQUENCE: 45

```
Asp Ile Gln Leu Thr Gln Ser Pro Ser Ser Met Ser Ala Ser Leu Gly
1               5                   10                  15

Asp Thr Val Thr Ile Thr Cys Leu Ala Ser Gln Asp Ile Gly Asp Tyr
                20                  25                  30

Leu Ser Trp Tyr Gln Gln Lys Pro Gly Lys Ser Pro Lys Val Met Val
            35                  40                  45

Tyr Gly Ala Thr Asn Leu Glu Asp Gly Val Pro Ser Arg Phe Ser Gly
    50                  55                  60

Ser Arg Ser Gly Ser Asp Tyr Ser Leu Thr Ile Asn Ser Leu Gly Tyr
65                  70                  75                  80

Asp Asp Glu Gly Ile Tyr His Cys His Gln Tyr Tyr Gln Tyr Pro Leu
                85                  90                  95

Thr Phe Gly Ser Gly Thr Lys Leu Glu Ile Lys Arg
            100                 105
```

<210> SEQ ID NO 46
<211> LENGTH: 121
<212> TYPE: PRT
<213> ORGANISM: Artificial Sequence
<220> FEATURE:
<223> OTHER INFORMATION: CD21-binding domain

<400> SEQUENCE: 46

```
Glu Val Gln Leu Gln Gln Ser Gly Ala Glu Leu Gly Lys Pro Gly Thr
1               5

```
                    20                  25                  30
Tyr Ile His Trp Val Asn Gln Arg Pro Gly Lys Gly Leu Glu Trp Ile
                35                  40                  45
Gly Arg Ile Asp Pro Ala Asn Gly Asp Thr Ile Tyr Ala Glu Lys Phe
         50                  55                  60
Lys Ser Lys Ala Thr Leu Thr Ala Asp Thr Ser Asn Thr Ala Tyr
 65                  70                  75                  80
Met Gln Leu Ser Gln Leu Lys Ser Asp Asp Thr Ala Ile Tyr Phe Cys
                 85                  90                  95
Ala Met Arg Met Val Gly Thr Gly Gly Tyr Ala Met Asp Ala Trp Gly
                100                 105                 110
Gln Gly Ala Ser Val Thr Val Ser Ser
                115                 120
```

<210> SEQ ID NO 47
<211> LENGTH: 111
<212> TYPE: PRT
<213> ORGANISM: Artificial Sequence
<220> FEATURE:
<223> OTHER INFORMATION: CD21-binding domain

<400> SEQUENCE: 47

```
Asp Ile Val Leu Thr Gln Ser Pro Ala Leu Ala Val Ser Pro Gly Gln
  1               5                  10                  15
Arg Ala Thr Ile Ser Cys Arg Ala Ser Gln Ser Val Ser Ile Ser Ser
                 20                  25                  30
Val Asn Leu Met Asn Trp Tyr Gln Gln Lys Pro Gly Gln Gln Pro Lys
                 35                  40                  45
Leu Leu Ile Tyr His Ala Ser Asn Leu Ala Ser Gly Ile Pro Thr Arg
         50                  55                  60
Phe Ser Gly Ser Gly Ser Gly Thr Asp Phe Thr Leu Thr Ile Asp Pro
 65                  70                  75                  80
Val Gln Ala Asp Asp Ile Ala Thr Tyr Tyr Cys Gln Gln Ser Arg Glu
                 85                  90                  95
Ser Pro Trp Thr Phe Gly Gly Gly Thr Lys Leu Glu Leu Lys Arg
                100                 105                 110
```

<210> SEQ ID NO 48
<211> LENGTH: 121
<212> TYPE: PRT
<213> ORGANISM: Artificial Sequence
<220> FEATURE:
<223> OTHER INFORMATION: CD21-binding domain

<400> SEQUENCE: 48

```
Val Gln Leu Gln Gln Ser Gly Ala Glu Leu Val Glu Pro Gly Ser Ser
  1               5                  10                  15
Val Lys Ile Ser Cys Lys Ala Ser Gly Tyr Thr Phe Thr Ser Asn Phe
                 20                  25                  30
Met His Trp Ile Arg Gln Gln Pro Gly Asn Gly Leu Glu Trp Ile Gly
                 35                  40                  45
Trp Val Tyr Arg Gly Asp Gly Asp Thr Glu Tyr Asn Gln Arg Phe Asn
         50                  55                  60
Gly Lys Ala Thr Leu Thr Ala Asp Glu Ser Ser Ser Thr Ala Tyr Ile
 65                  70                  75                  80
Gln Leu Ser Gly Leu Thr Ser Glu Asp Ser Ala Val Tyr Phe Cys Ala
                 85                  90                  95
```

```
Arg Gly Asp Ser Ser Gly Trp Gly Pro Asn Trp Phe Asp Ser Trp Gly
                100                 105                 110

Gln Gly Thr Leu Val Thr Val Ser Ser
        115                 120
```

<210> SEQ ID NO 49
<211> LENGTH: 108
<212> TYPE: PRT
<213> ORGANISM: Artificial Sequence
<220> FEATURE:
<223> OTHER INFORMATION: CD21-binding domain

<400> SEQUENCE: 49

```
Asp Val Gln Met Thr Gln Ser Pro Ala Ser Leu Ser Ala Ser Leu Gly
1               5                   10                  15

Glu Thr Val Thr Ile Glu Cys Arg Ala Ser Glu Asp Ile Tyr Ser Asn
            20                  25                  30

Leu Ala Trp Tyr Gln Gln Lys Pro Gly Asn Ser Pro Gln Leu Leu Ile
        35                  40                  45

Tyr Asp Ala Asn Ser Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Val Ala Ser Tyr Phe Cys Gln Gln Tyr Asn Asn Tyr Pro Leu
                85                  90                  95

Thr Phe Gly Ser Glu Thr Arg Leu Glu Ile Lys Arg
            100                 105
```

<210> SEQ ID NO 50
<211> LENGTH: 113
<212> TYPE: PRT
<213> ORGANISM: Artificial Sequence
<220> FEATURE:
<223> OTHER INFORMATION: CD21-binding domain

<400> SEQUENCE: 50

```
Gln Val Gln Leu Gln Gln Ser Gly Ala Gln Leu Val Lys Pro Gly Ser
1               5                   10                  15

Ser Val Lys Leu Ser Cys Lys Thr Ser Gly Phe Thr Phe Ser Ser Ser
            20                  25                  30

Tyr Ile Ser Trp Leu Lys Gln Ala Pro Gly Gln Ser Phe Glu Trp Ile
        35                  40                  45

Gly Asn Ile Phe Ala Gly Asp Gly Gly Pro Asn Tyr Ser Gln Lys Phe
    50                  55                  60

Lys Gly Lys Ala Thr Leu Thr Val Asp Thr Ser Ser Asn Thr Ala Tyr
65                  70                  75                  80

Met Asp Leu Ser Ser Leu Thr Ser Glu Asp Ser Ala Leu Tyr Phe Cys
                85                  90                  95

Ala Arg Pro Trp Ala Asn Trp Gly Gln Gly Thr Leu Val Thr Val Ser
            100                 105                 110

Ser
```

<210> SEQ ID NO 51
<211> LENGTH: 107
<212> TYPE: PRT
<213> ORGANISM: Artificial Sequence
<220> FEATURE:
<223> OTHER INFORMATION: CD21-binding domain

<400> SEQUENCE: 51

```
Glu Ile Val Leu Thr Gln Ser Pro Thr Thr Ala Ala Ser Pro Gly
1               5                   10                  15

Glu Lys Val Thr Ile Thr Cys Leu Ala Ser Ser Ala Ser Asn Met
            20                  25                  30

Phe Trp Tyr Gln Gln Lys Ser Gly Asp Ser Pro Lys Leu Leu Ile Tyr
            35                  40                  45

Ser Thr Ser Ser Leu Ala Ser Gly Val Pro Asp Arg Phe Ser Gly Ser
50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Leu Gln Arg Ser Ser Tyr Pro Trp Thr
                85                  90                  95

Phe Gly Gly Gly Thr Lys Leu Glu Leu Lys Arg
            100                 105
```

<210> SEQ ID NO 52
<211> LENGTH: 120
<212> TYPE: PRT
<213> ORGANISM: Artificial Sequence
<220> FEATURE:
<223> OTHER INFORMATION: CD21-binding domain

<400> SEQUENCE: 52

```
Glu Val Gln Leu Val Glu Thr Gly Gly Gly Leu Val Gln Pro Gly Lys
1               5                   10                  15

Ser Leu Lys Leu Thr Cys Ala Thr Ser Gly Phe Thr Phe Ser Thr Ala
            20                  25                  30

Trp Met His Trp Val Arg Gln Ser Pro Asp Lys Arg Leu Glu Trp Ile
            35                  40                  45

Ala Arg Ile Lys Asp Lys Ser Lys Asn Tyr Ala Thr Asp Tyr Val Glu
50                  55                  60

Ala Val Lys Gly Arg Phe Ser Ile Ser Arg Asp Asp Ser Lys Ser Ser
65                  70                  75                  80

Val Tyr Leu Gln Met Asn Ser Leu Lys Glu Glu Asp Thr Ala Thr Tyr
                85                  90                  95

Tyr Cys Thr Thr Gly Thr Tyr Arg Tyr Tyr Phe Asp Tyr Trp Gly Gln
            100                 105                 110

Gly Val Met Val Thr Val Ser Ser
            115                 120
```

<210> SEQ ID NO 53
<211> LENGTH: 107
<212> TYPE: PRT
<213> ORGANISM: Artificial Sequence
<220> FEATURE:
<223> OTHER INFORMATION: CD21-binding domain

<400> SEQUENCE: 53

```
Glu Ile Val Leu Thr Gln Ser Pro Thr Thr Ala Ala Ser Pro Gly
1               5                   10                  15

Glu Lys Val Thr Ile Thr Cys Leu Ala Asn Ser Ser Val Ser Asn Met
            20                  25                  30

Tyr Trp Tyr Gln Gln Lys Ser Gly Ala Ser Pro Lys Leu Leu Ile Tyr
            35                  40                  45

Ser Thr Ser Arg Leu Ala Ser Gly Val Pro Asp Arg Phe Ser Gly Ser
50                  55                  60

Gly Ser Gly Thr Ser Ser Ser Leu Thr Ile Asn Thr Met Glu Ala Glu
```

Asp Ala Ala Thr Tyr Tyr Cys Gln Gln Trp Ser Ser Asp Pro Pro Thr
            85                  90                  95

Phe Gly Ser Gly Thr Lys Leu Glu Leu Lys Arg
            100                 105

<210> SEQ ID NO 54
<211> LENGTH: 116
<212> TYPE: PRT
<213> ORGANISM: Artificial Sequence
<220> FEATURE:
<223> OTHER INFORMATION: CD21-binding domain

<400> SEQUENCE: 54

Val Gln Leu Gln Gln Ser Gly Ala Glu Leu Ala Lys Pro Gly Ser Ser
1               5                   10                  15

Val Lys Ile Ser Cys Lys Ala Ser Gly Tyr Thr Phe Thr Asn Tyr His
            20                  25                  30

Ile Thr Trp Ile Lys Gln Thr Thr Gly Gln Gly Leu Glu Tyr Val Gly
        35                  40                  45

Tyr Ile Asn Thr Gly Ser Gly Thr Thr Tyr Asn Glu Lys Phe Lys
    50                  55                  60

Gly Lys Ala Thr Leu Thr Val Asp Lys Ser Ser Ser Thr Ala Phe Met
65                  70                  75                  80

Gln Leu Ser Ser Leu Thr Pro Asp Asp Ser Ala Val Tyr Tyr Cys Ala
                85                  90                  95

Arg Leu Val Leu His Trp Phe Ala Tyr Trp Gly Gln Gly Thr Leu Val
            100                 105                 110

Thr Val Ser Ser
        115

<210> SEQ ID NO 55
<211> LENGTH: 113
<212> TYPE: PRT
<213> ORGANISM: Artificial Sequence
<220> FEATURE:
<223> OTHER INFORMATION: CD21-binding domain

<400> SEQUENCE: 55

Asp Ile Val Met Thr Gln Gly Ala Leu Pro Asn Pro Val Pro Ser Gly
1               5                   10                  15

Glu Val Ala Ser Ile Thr Cys Gln Ser Ser Lys Ser Leu Leu His Ser
            20                  25                  30

Asn Gly Lys Thr Tyr Leu Asn Trp Tyr Leu Gln Arg Pro Gly Gln Ser
        35                  40                  45

Pro Gln Leu Leu Ile Tyr Trp Met Ser Thr Arg Ala Ser Gly Val Ser
    50                  55                  60

Asp Arg Phe Ser Gly Ser Gly Ser Gly Thr Asp Phe Thr Leu Lys Ile
65                  70                  75                  80

Ser Ser Val Glu Ala Glu Asp Val Gly Val Tyr Tyr Cys Gln Gln Phe
                85                  90                  95

Leu Glu Tyr Pro Arg Thr Phe Gly Gly Gly Thr Lys Leu Glu Leu Lys
            100                 105                 110

Arg

<210> SEQ ID NO 56
<211> LENGTH: 15
<212> TYPE: PRT

```
<213> ORGANISM: Artificial Sequence
<220> FEATURE:
<223> OTHER INFORMATION: linker sequence

<400> SEQUENCE: 56

Gly Gly Gly Gly Ser Gly Gly Gly Gly Ser Gly Gly Gly Gly Ser
1               5                   10                  15

<210> SEQ ID NO 57
<211> LENGTH: 7
<212> TYPE: PRT
<213> ORGANISM: Artificial Sequence
<220> FEATURE:
<223> OTHER INFORMATION: Clone MP28132 VL CDR2

<400> SEQUENCE: 57

Asp Ala Asn Ser Leu Ala Asp
1               5

<210> SEQ ID NO 58
<211> LENGTH: 245
<212> TYPE: PRT
<213> ORGANISM: Artificial Sequence
<220> FEATURE:
<223> OTHER INFORMATION: scFv sequence

<400> SEQUENCE: 58

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Thr Phe Thr Ser Asn
            20                  25                  30

Phe Met His Trp Ile Lys Gln Gln Pro Gly Asn Gly Leu Glu Trp Ile
        35                  40                  45

Gly Trp Ile Ser Pro Gly Asp Gly Asp Thr Glu Tyr Asn Gln Lys Phe
    50                  55                  60

Asn Gly Lys Ala Thr Leu Thr Ala Asp Glu Ser Ser Ser Thr Ala Tyr
65                  70                  75                  80

Ile Gln Leu Ser Gly Leu Thr Ser Glu Asp Ser Ala Val Tyr Phe Cys
                85                  90                  95

Ala Arg Gly Asp Ser Ser Gly Trp Gly Pro Asn Trp Phe Asp Ser Trp
            100                 105                 110

Gly Gln Gly Thr Leu Val Thr Val Ser Gly Gly Gly Gly Ser Gly
        115                 120                 125

Gly Gly Gly Ser Gly Gly Gly Ser Asp Ile Gln Met Thr Gln Ser
    130                 135                 140

Pro Ser Ser Met Ser Ala Ser Leu Gly Asp Thr Val Thr Ile Thr Cys
145                 150                 155                 160

Leu Ala Ser Gln Asp Ile Gly Asn Tyr Leu Ser Trp Tyr Gln Gln Lys
                165                 170                 175

Pro Gly Lys Ser Pro Lys Leu Met Ile Tyr Asp Val Asn Asn Leu Glu
            180                 185                 190

Asp Gly Val Pro Ser Arg Phe Ser Gly Ser Arg Ser Gly Ser Asn His
        195                 200                 205

Ser Leu Thr Ile Asn Ser Leu Gly Tyr Asp Asp Glu Gly Ile Tyr His
    210                 215                 220

Cys Gln Gln Tyr Tyr Glu Tyr Pro Leu Thr Phe Gly Ser Gly Thr Lys
225                 230                 235                 240

Leu Glu Ile Lys Arg
                245
```

<210> SEQ ID NO 59
<211> LENGTH: 27
<212> TYPE: PRT
<213> ORGANISM: Artificial Sequence
<220> FEATURE:
<223> OTHER INFORMATION: transmembrane domain

<400> SEQUENCE: 59

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 60
<211> LENGTH: 112
<212> TYPE: PRT
<213> ORGANISM: Artificial Sequence
<220> FEATURE:
<223> OTHER INFORMATION: CD3-zeta endodomain

<400> SEQUENCE: 60

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 61
<211> LENGTH: 368
<212> TYPE: PRT
<213> ORGANISM: Artificial Sequence
<220> FEATURE:
<223> OTHER INFORMATION: 4-1BB and CD3-zeta endodomains

<400> SEQUENCE: 61

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
            165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
            210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu Arg
            245                 250                 255

Val Lys Phe Ser Arg Ser Ala Asp Ala Pro Ala Tyr Gln Gln Gly Gln
            260                 265                 270

Asn Gln Leu Tyr Asn Glu Leu Asn Leu Gly Arg Arg Glu Glu Tyr Asp
            275                 280                 285

Val Leu Asp Lys Arg Arg Gly Arg Asp Pro Glu Met Gly Gly Lys Pro
            290                 295                 300

Gln Arg Arg Lys Asn Pro Gln Glu Gly Leu Tyr Asn Glu Leu Gln Lys
305                 310                 315                 320

Asp Lys Met Ala Glu Ala Tyr Ser Glu Ile Gly Met Lys Gly Glu Arg
            325                 330                 335

Arg Arg Gly Lys Gly His Asp Gly Leu Tyr Gln Gly Leu Ser Thr Ala
            340                 345                 350

Thr Lys Asp Thr Tyr Asp Ala Leu His Met Gln Ala Leu Pro Pro Arg
            355                 360                 365

<210> SEQ ID NO 62
<211> LENGTH: 152
<212> TYPE: PRT
<213> ORGANISM: Artificial Sequence
<220> FEATURE:
<223> OTHER INFORMATION: CD28 and CD3-zeta endodomains

<400> SEQUENCE: 62

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser Arg Val Lys Phe Ser Arg Ser Ala
            35                  40                  45

Asp Ala Pro Ala Tyr Gln Gln Gly Gln Asn Gln Leu Tyr Asn Glu Leu
        50                  55                  60

Asn Leu Gly Arg Arg Glu Glu Tyr Asp Val Leu Asp Lys Arg Arg Gly
65                  70                  75                  80

Arg Asp Pro Glu Met Gly Gly Lys Pro Arg Arg Lys Asn Pro Gln Glu
            85                  90                  95

Gly Leu Tyr Asn Glu Leu Gln Lys Asp Lys Met Ala Glu Ala Tyr Ser
            100                 105                 110

```
Glu Ile Gly Met Lys Gly Glu Arg Arg Gly Lys Gly His Asp Gly
        115                 120                 125

Leu Tyr Gln Gly Leu Ser Thr Ala Thr Lys Asp Thr Tyr Asp Ala Leu
    130                 135                 140

His Met Gln Ala Leu Pro Pro Arg
145                 150

<210> SEQ ID NO 63
<211> LENGTH: 188
<212> TYPE: PRT
<213> ORGANISM: Artificial Sequence
<220> FEATURE:
<223> OTHER INFORMATION: CD28, OX40 and CD3-zeta endodomains

<400> SEQUENCE: 63

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser Arg Asp Gln Arg Leu Pro Pro Asp
        35                  40                  45

Ala His Lys Pro Pro Gly Gly Gly Ser Phe Arg Thr Pro Ile Gln Glu
    50                  55                  60

Glu Gln Ala Asp Ala His Ser Thr Leu Ala Lys Ile Arg Val Lys Phe
65                  70                  75                  80

Ser Arg Ser Ala Asp Ala Pro Ala Tyr Gln Gln Gly Gln Asn Gln Leu
                85                  90                  95

Tyr Asn Glu Leu Asn Leu Gly Arg Arg Glu Glu Tyr Asp Val Leu Asp
                100                 105                 110

Lys Arg Arg Gly Arg Asp Pro Glu Met Gly Gly Lys Pro Arg Arg Lys
            115                 120                 125

Asn Pro Gln Glu Gly Leu Tyr Asn Glu Leu Gln Lys Asp Lys Met Ala
        130                 135                 140

Glu Ala Tyr Ser Glu Ile Gly Met Lys Gly Glu Arg Arg Arg Gly Lys
145                 150                 155                 160

Gly His Asp Gly Leu Tyr Gln Gly Leu Ser Thr Ala Thr Lys Asp Thr
                165                 170                 175

Tyr Asp Ala Leu His Met Gln Ala Leu Pro Pro Arg
            180                 185

<210> SEQ ID NO 64
<211> LENGTH: 4
<212> TYPE: PRT
<213> ORGANISM: Artificial Sequence
<220> FEATURE:
<223> OTHER INFORMATION: ITAM (immunoreceptor tyrosine-based activation
      motif)
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa may be Leu or Ile

<400> SEQUENCE: 64

Tyr Xaa Xaa Xaa
1
```